(12) United States Patent
Gamsey et al.

(10) Patent No.: US 10,383,557 B2
(45) Date of Patent: *Aug. 20, 2019

(54) OXYGEN SENSORS

(71) Applicant: Profusa, Inc., South San Francisco, CA (US)

(72) Inventors: Soya Gamsey, San Francisco, CA (US); Natalie Wisniewski, San Francisco, CA (US); Kristen Helton, Seattle, WA (US); William A. McMillan, La Honda, CA (US)

(73) Assignee: Profusa, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/830,798

(22) Filed: Dec. 4, 2017

(65) Prior Publication Data

US 2018/0184956 A1 Jul. 5, 2018

Related U.S. Application Data

(63) Continuation of application No. 15/189,448, filed on Jun. 22, 2016, now Pat. No. 9,867,560, which is a continuation of application No. 14/209,252, filed on Mar. 13, 2014, now Pat. No. 9,375,494.

(60) Provisional application No. 61/784,925, filed on Mar. 14, 2013.

(51) Int. Cl.
| | |
|---|---|
| *A61B 5/1455* | (2006.01) |
| *A61K 49/00* | (2006.01) |
| *A61B 5/145* | (2006.01) |
| *C07F 15/00* | (2006.01) |
| *C09K 11/06* | (2006.01) |
| *C12Q 1/54* | (2006.01) |
| *G01N 33/497* | (2006.01) |
| *A61B 5/00* | (2006.01) |

(52) U.S. Cl.
CPC ...... *A61B 5/14552* (2013.01); *A61B 5/14532* (2013.01); *A61K 49/0036* (2013.01); *A61K 49/0054* (2013.01); *A61K 49/0073* (2013.01); *C07F 15/0066* (2013.01); *C09K 11/06* (2013.01); *C12Q 1/54* (2013.01); *G01N 33/497* (2013.01); *A61B 5/0059* (2013.01); *A61B 2503/40* (2013.01); *C09K 2211/185* (2013.01); *G01N 2333/904* (2013.01)

(58) Field of Classification Search
CPC ....... A61K 49/00; A61K 31/555; A61B 5/145
See application file for complete search history.

(56) References Cited

U.S. PATENT DOCUMENTS

| | | | |
|---|---|---|---|
| 5,220,036 A | 6/1993 | King | |
| 5,242,835 A | 9/1993 | Jensen | |
| 5,371,122 A | 12/1994 | Kawahara et al. | |
| 5,487,885 A | 1/1996 | Sovak et al. | |
| 5,837,865 A | 11/1998 | Vinogradov et al. | |
| 6,013,122 A | 1/2000 | Klitzman et al. | |
| 6,274,086 B1 | 8/2001 | Wilson et al. | |
| 6,362,175 B1 | 3/2002 | Vinogradov et al. | |
| 6,794,195 B2 | 9/2004 | Colvin, Jr. | |
| 7,060,503 B2 | 6/2006 | Colvin, Jr. | |
| 7,939,332 B2 | 5/2011 | Colvin, Jr. | |
| 9,375,494 B2 | 6/2016 | Gamsey et al. | |
| 9,650,566 B2 | 5/2017 | Gamsey et al. | |
| 9,867,560 B2 | 1/2018 | Gamsey et al. | |
| 2007/0110672 A1 | 5/2007 | Bellott et al. | |
| 2008/0075752 A1 | 3/2008 | Ratner et al. | |
| 2008/0311304 A1 | 12/2008 | Thompson et al. | |
| 2010/0303772 A1 | 12/2010 | McMillan et al. | |
| 2012/0165435 A1 | 6/2012 | Santhanam et al. | |
| 2012/0265034 A1* | 10/2012 | Wisniewski | A61B 5/14532 600/309 |
| 2013/0004785 A1 | 1/2013 | Carlson et al. | |
| 2013/0041200 A1 | 2/2013 | Sorokin et al. | |
| 2014/0286875 A1 | 9/2014 | Gamsey et al. | |
| 2016/0374601 A1 | 12/2016 | Gamsey et al. | |
| 2016/0376501 A1 | 12/2016 | Gamsey et al. | |

FOREIGN PATENT DOCUMENTS

| | | |
|---|---|---|
| EP | 0352610 A2 | 1/1990 |
| WO | WO 2012/027593 | 3/2012 |
| WO | WO 2014/160258 | 10/2014 |

OTHER PUBLICATIONS

Supplementary European Search Report for European Application No. 14775010.3, dated Sep. 30, 2016, 11 pages.
International Search Report and Written Opinion for International Application No. PCT/US2014/026183, dated Jul. 14, 2014, 11 pages.
Alexeev et al., "High ionic strength glucose-sensing photonic crystal," Anal. Chem., 75:2316-2323 (2003).
Badylak et al., "Immune response to biologic scaffold materials," Seminars in Immunology, 20(2):109-116 (2008).
Borisov, S. M. et al., "Red light-excitable oxygen sensing materials based on platinum(II) and palladium(II) benzoporphyrins," Analytical Chemistry, 80(24):9435-9442 (Dec. 2008).
Braun et al., "Comparison of tumor and normal tissue oxygen tension measurements using oxylite or microelectrodes in rodents," Am. J. Physiol. Heart Circ. Physiol., 280(6):H2533-H2544 (2001).
Bridges et al., "Chronic inflammatory responses to microgel-based implant coatings," J Biomed. Mater. Res. A., 94(1):252-258 (2010).
Dunphy, I. et al., "Oxyphor R2 and G2: phosphors for measuring oxygen by oxygen-dependent quenching phosphorescence," Anal. Biochem., 310:191-198 (2002).
Hutter, L. H. et al., "Robust optical oxygen sensors based on polymer-bound NIR-emitting platinum(II)-benzoporphyrins," J. Mat. Chem. C., 36:7589-7598 (Jul. 2014).
Isenhath et al., "A mouse model to evaluate the interface between skin and a percutaneous device," J Biomed. Mater. Research, 83A:915-922 (2007).

(Continued)

*Primary Examiner* — Michael G. Hartley
*Assistant Examiner* — Jagadishwar R Samala
(74) *Attorney, Agent, or Firm* — Cooley LLP

(57) ABSTRACT

Oxygen sensing luminescent dyes, polymers and sensors comprising these sensors and methods of using these sensors and systems are provided.

18 Claims, 12 Drawing Sheets

(56) References Cited

OTHER PUBLICATIONS

Ju, Y. M. et al., "A novel porous collagen scaffold around an implantable biosensor for improving biocompatibility. I. In vitrol in vivo stability of the scaffold and in vitro sensitivity of the glucose sensor with scaffold," J Biomed. Mater. Research, 87A:136-146 (2008), Available online Dec. 17, 2007.

Kaehr et al., "Multiphoton fabrication of chemically responsive protein hydrogels for microactuation," PNAS USA, 105(26):8850-8854 (2008).

Kasprzak, S. E., "Small-scale polymer structures enabled by thiol-ene copolymer systems," Doctoral Dissertation, Georgia Institute of Technology, May 2009.

Kloxin, A. M. et al., "Photodegradable hydrogels for dynamic tuning of physical and chemical properties," Science, 324:59-63 (2009).

Marshall et al., "Biomaterials with tightly controlled pore size that promote vascular in-growth," ACS Polymer Preprints, 45(2):100-101 (2004).

Nielson, R. et al., "Microreplication and design of biological architectures using dynamicmask multiphoton lithography," Small, 5(1):120-125 (2009).

Ostendorf, A. et al., "Two-photon polymerization: a new approach to micromachining," Photonics Spectra, 40(10):72-79 (2006).

Ozdemir et al., "Axial pattern composite prefabrication of high-density porous polyethylene: experimental and clinical research," Plast. Reconstr. Surg., 115(1):183-196 (2005).

Phelps et al., "Bioartificial matrices for therapeutic vascularization," PNAS USA, 107(8):3323-3328 (2010).

Quaranta, M. et al., "Indicators for optical oxygen sensors," Bioanalytical Reviews, 4(2-4):115-157 (Nov. 2012).

Rietveld, I. B. et al., "Dendrimers with tetrabenzoporphyrin cores: near infra-red phosphors for in vivo oxygen imaging," Tetrahedron, 59, 3821-3831, 2003.

Sanders et al., "Tissue response to single-polymer fibers of varying diameters: evaluation of fibrous encapsulation and macrophage density," J Biomed. Mater. Research, 52:231-237 (2000).

Sanders et al., "Tissue response to microfibers of different polymers: polyester, polyethylene, polylactic acid, and polyurethane," J Biomed. Mater. Research, 62(2):222-227 (2002).

Sanders et al., "Fibrous encapsulation of single polymer microfibers depends on their vertical dimension in subcutaneous tissue," J Biomed. Mater. Research, 67A:1181-1187 (2003).

Sanders et al., "Relative influence of polymer fiber diameter and surface charge on fibrous capsule thickness and vessel density for single-fiber implants," J Biomed. Mater. Research, 65A:462-467 (2003).

Sanders et al., "Polymer microfiber mechanical properties: a system for assessment and investigation of the link with fibrous capsule formation," J Biomed. Mater. Research, 67A:1412-1416 (2003).

Sanders et al., "Small fiber diameter fibro-porous meshes: tissue response sensitivity to fiber spacing," J Biomed Mater Research, 72A:335-342 (2005).

Sanders et al., "Fibro-porous meshes made from polyurethane micro-fibers: effects of surface charge on tissue response," Biomaterials, 26(7):813-818 (2005).

Tian et al., "Dually fluorescent sensing of PH and dissolved oxygen using a membrane made from polymerizable sensing monomers," Sensors and Actuators B, 147:714-722 (2010).

Tian et al., "Influence of matrices on oxygen sensing of three-sensing films with chemically conjugated platinum porphyrin probes and preliminary application for monitoring of oxygen consumption of *Escherichia coli* (*E. coli*)," Sensors and Actuators B, 150:579-587 (2010).

Tian, Y. et al., "A New Cross-linkable Oxygen Sensor Covalently Bonded into Poly(2-hydroxyethyl methacrylate)-co-Polyacrylamide Thin Film for Dissolved Oxygen Sensing," Chemistry Materials, 22(6):2069-2078 (2010).

Vinogradov, S. A. et al., "Pd tetrabenzoporphyrin-dendrimers: near-infrared phosphors for oxygen measurements by phosphorescense quenching," Proc. SPIE, 4626:193-200 (2002).

Menard et al., "Synthesis of tetraglucosyl-and tetrapolyamine-tetrabenzoporphyrin conjugates for an application in PDT," Bioorganic & Medicinal Chemistry, 17 (2009) 7647-7657, 11 pages.

Extended European Search Report for European Application No. 18200504.1, dated Apr. 8, 2019, 13 pages.

\* cited by examiner

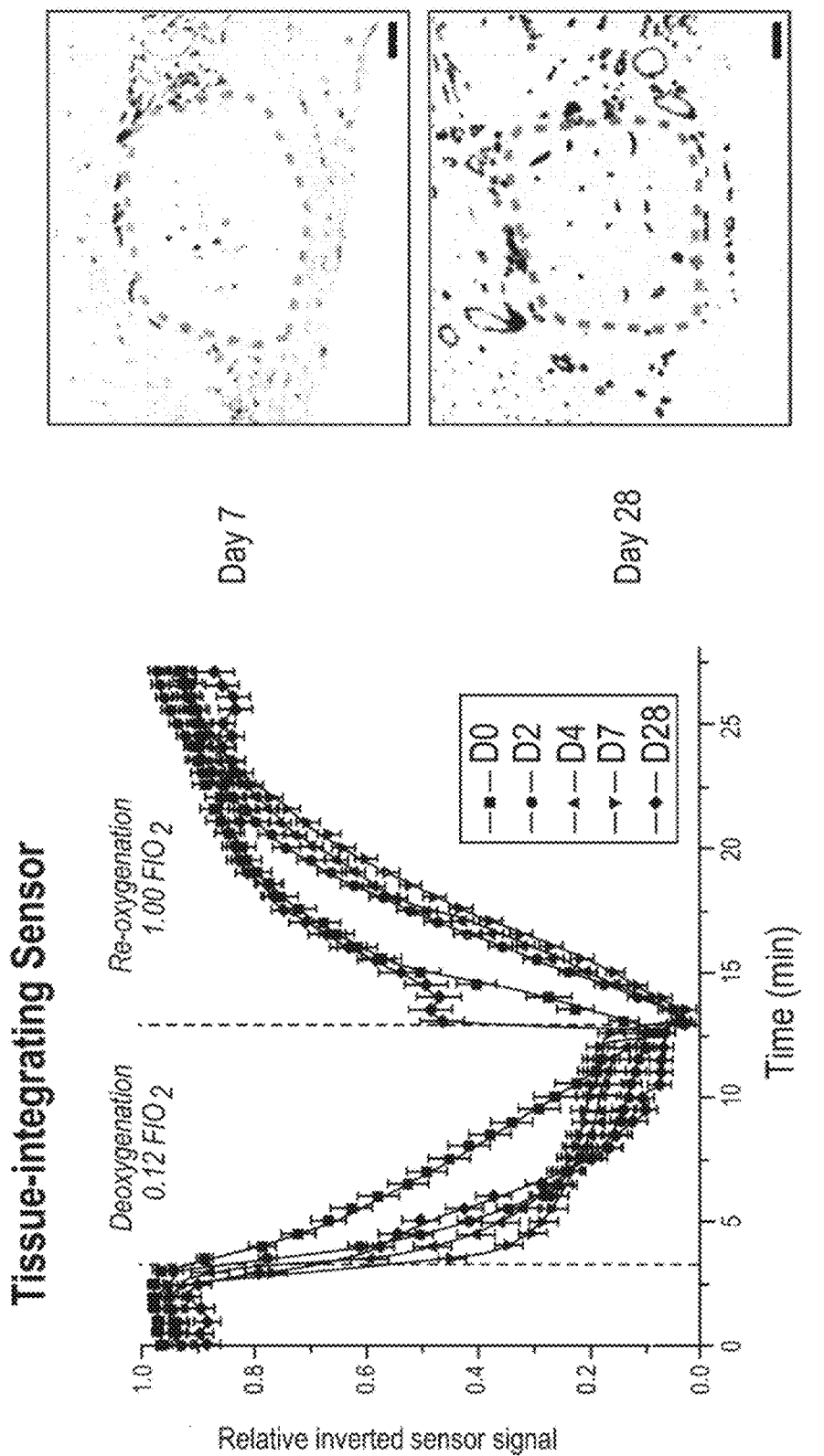

OXYGEN SENSORS

CROSS-REFERENCE TO RELATED APPLICATIONS

This application is a continuation of U.S. patent application Ser. No. 15/189,448, filed Jun. 22, 2016, which is a continuation of U.S. patent application Ser. No. 14/209,252, filed Mar. 13, 2014, now, U.S. Pat. No. 9,375,494, which claims the benefit of U.S. provisional patent application 61/784,925, filed on Mar. 14, 2013, titled "Oxygen Sensors", the disclosure of each of which is hereby incorporated by reference in its entirety.

TECHNICAL FIELD

The present disclosure is in the field of luminescent dyes, polymers and biosensors.

BACKGROUND

Diagnosis, treatment and management of some medical conditions require monitoring of oxygen concentration in the afflicted organ or tissue. For example, Peripheral Arterial Disease (PAD), a disease that is characterized by plaque buildup in arteries that carry blood to the extremities, head, or organs, if left untreated, can lead to complete blockage of lower extremity arteries and requires either open bypass surgery or endovascular intervention. Annually, at least 140,000 such revascularization procedures are conducted in the US alone to restore blood flow to ischemic tissues. Thus, ensuring that blood and oxygen flow are adequately restored and maintained during and after the revascularization technique is highly desirable. Current monitoring methods are expensive, cumbersome, time consuming, and do not provide accurate, continuous tissue oxygenation information. Thus, there is clearly a need for a better long-term oxygen tissue monitoring system. Doing so non-invasively with minimal user maintenance is essential, and sensor longevity of days to months is crucial in actual user environments.

Such real-time, continuous measurement of oxygen concentration (partial pressure) in tissues can be achieved by the use of sensors inserted or implanted into the tissue and measuring the signal generated by the sensor by a device located outside the body. Luminescence provides a useful tool for the design of such sensors. Luminescent oxygen sensors are based on the phenomenon that oxygen has a quenching effect on the molecular luminescence of various chemical compounds and that this effect can be employed for measuring oxygen concentrations (partial pressure) in vivo. The sensors, which are monitored optically through the skin, require a highly stable dye with excitation and emission spectra in the near-infrared (NIR) optical window of the skin. These dye properties are crucial for the successful design of a luminescent oxygen sensor that can be implanted deep into tissue. Monitoring non-invasively through the skin requires the use of dyes with excitation and emission wavelengths in the optical window of the skin (approximately 550 to 1000 nm) to minimize light scattering and absorbance, and achieve a high signal-to-noise ratio. However, commercially available NIR dyes can be prone to photobleaching. Palladium porphyrins, such as tetracarboxyphenyl porphyrin (Pd-TCPP) have a very large Stokes shift and emission in the NIR. However, they unfortunately require excitation with green light (525 nm), which is largely absorbed by the skin and the underlying tissue. Additionally, currently available sensors, made of rigid materials that vastly differ from the mechanical properties of tissue in which they are implanted, are bulky and inconvenient, and induce a series of biological events upon implantation that ultimately culminate in the formation of a fibrous capsule that walls it off from the body.

Thus, until the present invention there remains a clear need in the art to provide improved stable, near-IR luminescent compounds and sensors for direct, rapid and accurate measurement of oxygen levels in tissue, particularly in vivo.

SUMMARY

Disclosed herein are luminescent dyes, polymers comprising said dyes, and sensors comprising the polymers of the present invention.

In one embodiment, the present invention relates to a compound of Formula 1:

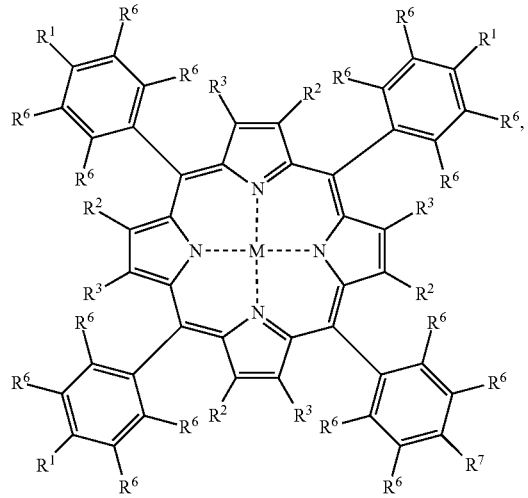

wherein:
M is H, Pd, Zn, Pt, Gd or Yb;
each $R^1$ is same or different and independently C(O)X—$(CH_2)_n$—YC(O)C($R^4$)$CH_2$, C(O)X—$(CH_2CH_2O)_m$$CH_2CH_2$—YC(O)C($R^4$)$CH_2$ or COOH;
$R^7$ is C(O)X—$(CH_2)_n$—YC(O)C($R^4$)$CH_2$ or C(O)X—$(CH_2CH_2O)_m$$CH_2CH_2$—YC(O)C($R^4$)$CH_2$;
$R^2$ and $R^3$ are hydrogen or are fused, in each case, to form a cycloalkenyl, aryl, or heteroaryl group;
X is O or $NR^5$;
Y is O or NH;
$R^5$ and $R^4$ are independently H or C1-C4 alkyl;
each $R^6$ is the same or different and independently H or F;
n is 1-10; and
m is 1-300.

In another aspect, the present invention relates to a polymer comprising as a monomer repeat unit, the residue of the compound of Formula 1. The polymers provided herein can be luminescent biocompatible hydrogels.

In further embodiments, the present invention relates to various luminescent sensors comprising the polymers provided herein for detecting an analyte, e.g., oxygen, in vivo or in vitro. The sensors can be in the form of a powder, fabric (e.g., wound dressing), sutures, needle, rod, disk or any other suitable form.

In another aspect, the luminescent sensors provided herein are tissue-integrating or comprise a tissue-integrating scaffold and produce a detectable signal in the presence of the analyte; and further wherein the sensors provide detection of the analyte when placed (e.g., implanted) into the tissue of a subject. The tissue-integrating sensors as described herein can provide long-term detection of the analyte(s).

BRIEF DESCRIPTION OF THE DRAWINGS

FIG. 2 shows the intensity of NIR Pd-BP and green-ex Pd-TCPP subcutaneous hydrogel implants measured in a rat carcass. Pd-BP is significantly brighter than TCPP hydrogel due to the NIR excitation and emission wavelengths, which allow much greater light penetration into the skin, enabling deeper sensor placement.

FIG. 11C depicts porous, tissue-integrating sensor response to deoxygenation (0.12 FIO2) and re-oxygenation (1.00 FIO2).

FIG. 11D shows fluorescent micrographs of porous, tissue-integrating sensors and surrounding tissue samples at 7 and 28 days after implantation.

DETAILED DESCRIPTION

Figure 1:
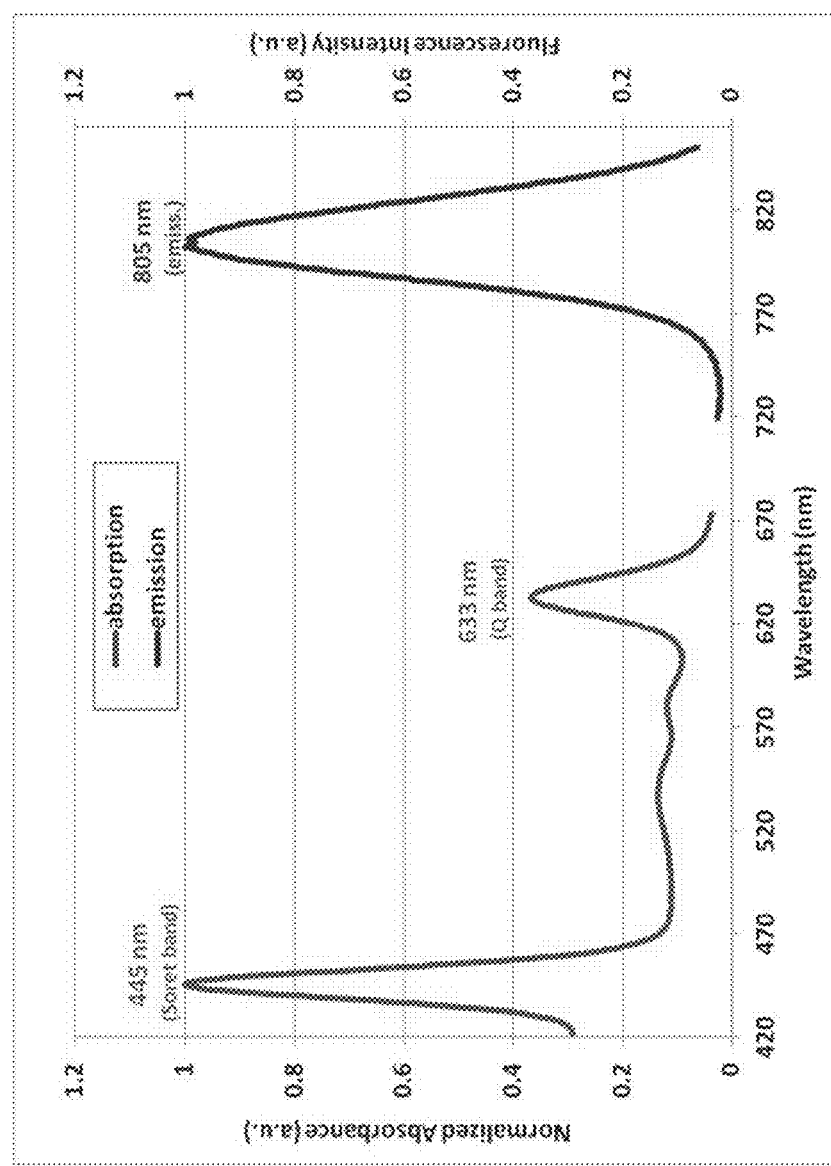
FIG. 1 depicts Compound 2 (Pd-BP) absorption and emission spectra. Spectra were taken of covalently bound Pd-BP in pHEMA hydrogel. Excitation at 633 nm gave 805 nm emission, confirming shift into the NIR.

Described herein are polymerizable luminescent dyes useful for incorporation into polymers and polymers comprising as monomeric units residues of the dyes of the present invention. The dyes and the polymers are useful, for example, in sensing and imaging applications, for example, accurate and optionally long term measurements of oxygen in vivo and in vitro.

Additionally, described herein are sensors comprising the polymers of the present invention. The sensors can be implanted into a tissue of a subject and used for long-term or short-term continuous and semi-continuous collection of data of various biochemical analytes, optionally without the use of implantable hardware of any type and/or enzymatic and electrochemical detection methods. In one aspect, the sensors are tissue integrating, e.g., allow capillaries to grow in close proximity to all regions of the sensor (e.g., on the surface and inside), which results in accurate analyte measurements, including over long term. In another aspect, in addition to the luminescent dyes and/or the polymers of the present invention, the sensors comprise an oxidase, such as, but not limited to, glucose oxidase, and the luminescent dyes and/or their residues incorporated as monomeric units into the polymers measure the consumption of oxygen by the oxidase, thus, the sensors can provide detection of a number of analytes other than oxygen, such as, but not limited to, glucose.

Advantages of the dyes and luminescent polymers provided herein include, but are not limited to: (1) excitation and emission wavelengths in the optical window of the skin (approximately 550 nm to 1000 nm) allowing detection of analytes deep within a tissue or an organ; (2) high signal-to-noise ratio; (3) large Stokes shifts and emission; (4) photostablity, e.g., the dyes and/or polymers do not undergo rapid photobleaching.

Advantages of the sensors described herein include, but are not limited to: (1) providing devices that generate stable signal over a long period of time (e.g., greater than a week, greater than a month, greater than 6 months), (2) providing devices that are placed or implanted and integrate into the subject's tissue (e.g., through tissue and/or capillary in-growth); (3) providing devices which can be implanted through syringe injection or trocar injection, meaning that no surgery is required to put the sensing media in place in the body; (4) providing devices that do not include sensor electronics in the body; (5) providing devices that accurately assess analyte (e.g., oxygen) concentration for long periods of time (e.g., greater than a week, typically weeks, months or years) and/or (6) providing devices of small dimensions which will give result in increased patent comfort and better acceptance by the body.

It must be noted that, as used in this specification and the appended claims, the singular forms "a", "an", and "the" include plural referents unless the content clearly dictates otherwise. Thus, for example, reference to a sensor comprising "a sensing moiety" includes devices comprising of two or more sensing moieties. Likewise, reference to "an analyte" refers to two or more analytes.

DEFINITIONS

The term "tissue integrating" refers to a material (e.g., scaffold) which, when integrated into living tissue remains in close proximity with the blood vessels of the tissue (e.g., capillaries).

By "long-term" is meant that the implant senses the analyte for greater than about 7 days, for example weeks, months, or years.

By "biodegradable" or "bioabsorbable" is meant that the material is capable of being broken down by the subject's body over a period of time, ranging from days to weeks to months or years.

By "hydrogel" is meant a material that absorbs a solvent (e.g. water), undergoes rapid swelling without discernible dissolution, and maintains three-dimensional networks capable of reversible deformation.

The term "stimuli-responsive" refers to substances, e.g., polymers, that change their physical state, e.g., undergo a phase transition, when exposed to an external stimulus or according to the environment they are in. Non-limiting examples of such polymers are "smart polymers" (Kumar A. et al., Smart polymers: Physical forms and bioengineering applications. *Prog. Polym. Sci.* 32 (2007) 1205-1237).

A. Luminescent NIR Dyes

In one aspect, this invention provides a compound of Formula 1:

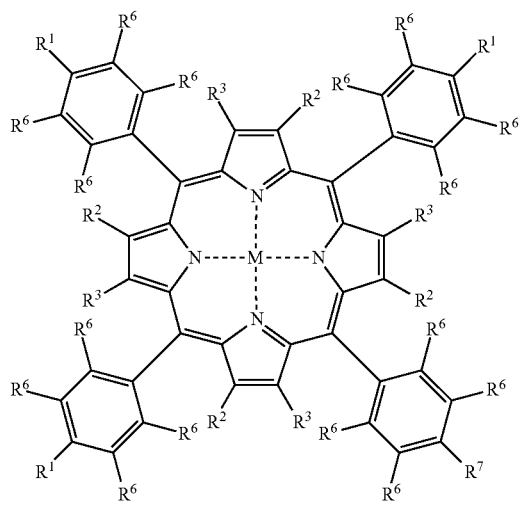

wherein

M is H, Pd, Zn, Pt, Gd or Yb;

each $R^1$ is same or different and independently $C(O)X—(CH_2)_n—YC(O)C(R^4)CH_2$, $C(O)X—(CH_2CH_2O)_m CH_2CH_2—YC(O)C(R^4)CH_2$ or COOH;

$R^7$ is $C(O)X—(CH_2)_n—YC(O)C(R^4)CH_2$ or $C(O)X—(CH2CH2O)m CH2CH2-YC(O)C(R4)CH2$;

$R^2$ and $R^3$ are hydrogen or are fused, in each case, to form a cycloalkenyl, aryl, or heteroaryl group;

X is O or $NR^5$;

Y is O or NH;

$R^5$ and $R^4$ are independently H or C1-C4 alkyl;

each $R^6$ is same or different and, independently, H or F;

n is 1-10; and m is 1-300.

In one embodiment, M is Pd. In another embodiment, $R^1$ and $R^7$ are both $C(O)NH(CH_2)_2OC(O)C(CH_3)CH_2$. In another embodiment, $R_1$ is $C(O)NH(CH_2)_2OC(O)C(CH_3)CH_2$ and $R^7$ is COOH. In yet another embodiment, two of the $R^1$ are $C(O)NH(CH_2)_2OC(O)C(CH_3)CH_2$, one of the $R^1$ is COOH and $R^7$ is COOH. In another embodiment, one of the $R^1$ is $C(O)NH(CH_2)_2OC(O)C(CH_3)CH_2$, two of the $R^1$ are COOH, and $R^7$ is COOH. In one embodiment, all $R^1$ and $R^7$ are COOH.

In another embodiment, $R^1$ and $R^7$ are both $C(O)X—(CH_2CH_2O)_mCH_2CH_2—YC(O)C(R_4)CH_2$. In another embodiment, $R^1$ is $C(O)X—(CH_2CH_2O)_mCH_2CH_2—YC(O)C(R_4)CH_2$ and $R^7$ is COOH. In yet another embodiment, two of the $R^1$ are $C(O)X—(CH_2CH_2O)_mCH_2CH_2—YC(O)C(R_4)CH_2$, one of the $R^1$ is COOH and $R^7$ is COOH. In another embodiment, one of the $R^1$ is $C(O)X—(CH_2CH_2O)_mCH_2CH_2—YC(O)C(R_4)CH_2$, two of the $R^1$ are COOH, and $R^7$ is COOH. In one embodiment, all $R^1$ and $R^7$ are COOH.

In another embodiment, $R^1$ and $R^7$ are both $C(O)X—(CH_2)_n—YC(O)C(R^4)CH_2$. In another embodiment, $R^1$ is $C(O)X—(CH_2)_n—YC(O)C(R^4)CH_2$ and $R_7$ is COOH. In yet another embodiment, two of the $R_1$ are $C(O)X—(CH2)_n—YC(O)C(R^4)CH_2$, one of the $R^1$ is COOH and $R^7$ is COOH. In another embodiment, one of the $R_1$ is $C(O)X—(CH_2)—YC(O)C(R^4)CH_2$, two of the $R^1$ are COOH, and $R^7$ is COOH. In one embodiment, all $R^1$ and $R^7$ are COOH.

In one embodiment, $R^2$ and $R^3$ are fused to form a heteroaryl group. In one embodiment, $R^2$ and $R^3$ are fused to form a cycloalkenyl group. In one embodiment, $R^2$ and $R^3$ are fused to form a tetracyclohexeno group. In one embodiment, $R^2$ and $R^3$ are fused to form an aryl group. In one embodiment, the aryl group is perfluorinated. In one embodiment, $R^2$ and $R^3$ are fused to form a benzo group. In another embodiment, $R^2$ and $R^3$ are fused to form a naphtho group.

In one embodiment, $R^1$ comprises an oligoethyene glycol linker having 2-300 ethylene units. In another embodiment, $R^7$ comprises an oligoethyene glycol linker having 2-300 ethylene units.

In one specific embodiment, M is Pd, $R^1$ and $R^7$ are both $C(O)NH(CH_2)_2OC(O)C(CH_3)CH_2$, and R2 and R3 are H.

In one specific embodiment, M is Pd, $R^1$ and $R^7$ are both $C(O)NH(CH_2)_2OC(O)C(CH_3)CH_2$, and $R^2$ and $R^3$ are fused to form a benzene ring.

In one embodiment, the compound of Formula 1 is a near-IR luminescent dye. In one embodiment, the compound of Formula 1 has an absorption maximum between 500 nm and 800 nm. In one specific embodiment, the compound of Formula 1 has an absorption maximum between 500 nm and 700 nm. In one embodiment, the compound of Formula 1 has an emission maximum between 500 and 1000 nm. In one embodiment, the compound of Formula 1 has an emission maximum between 650 and 900 nm. In one specific embodiment, the compound of Formula 1 has an emission maximum between 800 and 900 nm. In one embodiment, the compound of Formula 1 of the present invention is photostable and has excitation and emission spectra in the NIR optical window of the skin.

For example, in a preferred embodiment, as illustrated by FIG. 1, the Compound 2 of Formula 2 has an absorption maximum at 633 nm and an emission maximum at 805 nm when co-polymerized with HEMA into a hydrogel.

Formula 2

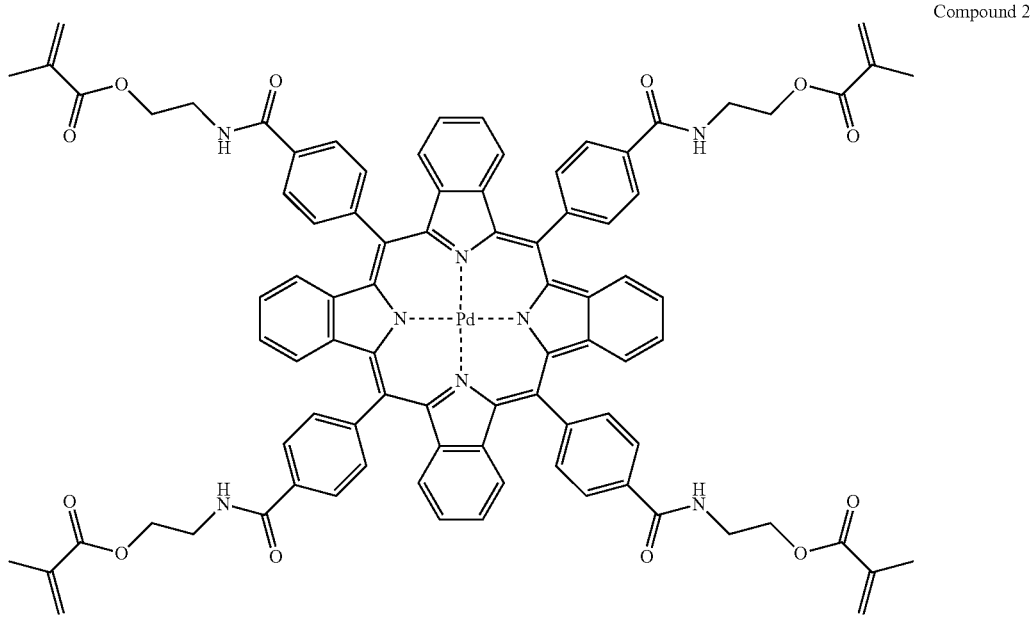

Compound 2

In some embodiments, the dyes of the present invention are encapsulated into a solid, oxygen-impermeable nanosphere. The nanospheres can be used for luminescent, non-oxygen sensitive applications.

B. Polymers

The fluorescent dyes of the present invention comprise polymerizable groups, e.g., residue of acrylic or methacrylic acid, and can be co-polymerized with other monomers to provide polymers comprising near-IR luminescent groups. When the compounds have 2 or more polymerizable groups, the polymers obtained from their co-polymerization with other monomers can be crosslinked. Alternatively, another crosslinking monomer can be added into the polymerization mixture to achieve a higher degree of crosslinking of the resulting polymer.

Polymers described herein can be prepared in any suitable manner. Suitable synthetic methods used to produce the polymers provided herein include, by way of non-limiting example, cationic, anionic and free radical polymerization. In certain embodiments, polymer synthesis is performed neat or in any suitable solvent. Suitable solvents include, but are not limited to, pentane, hexane, dichloromethane, chloroform, water, ethylene glycol, propylene glycol, DMSO or dimethyl formamide (DMF). In certain embodiments, the polymer synthesis is performed at any suitable reaction temperature, including, e.g., from about −50° C. to about 100° C., or from about 0° C. to about 70° C.

Preferably the polymers are prepared by the means of a free radical polymerization. When a free radical polymerization process is used, (i) the monomer, (ii) optionally, the co-monomer(s), and (iii) an optional source of free radicals are provided to trigger a free radical polymerization process. In some embodiments, the source of free radicals is optional because some monomers may self-initiate upon heating at high temperature. In certain instances, after forming the polymerization mixture, the mixture is subjected to polymerization conditions. Such conditions are optionally varied to any suitable level and include, by way of non-limiting example, temperature, pressure, light, atmosphere, ratios of starting components used in the polymerization mixture and reaction time. The polymerization is carried out in any suitable manner, including, e.g., in solution, dispersion, suspension, emulsion or bulk.

In some embodiments, initiators are present in the reaction mixture. Any suitable initiator is optionally utilized if useful in the polymerization processes described herein. Such initiators include, by way of non-limiting example, one or more of alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, or azo compounds. In specific embodiments, benzoylperoxide (BPO) and/or AIBN are used as initiators.

In some embodiments, polymerization processes are carried out in a controlled (living) mode. Preferred controlled (living) polymerization processes include reversible addition-fragmentation chain transfer (RAFT) polymerization processes and Atom Transfer Radical Polymerization (ATRP).

In certain embodiments, the polymer of the present invention is a hydrogel. For example, the hydrogel can be prepared by reacting hydroxyethyl methacrylate (HEMA), to form poly(hydroxyethyl methacrylate), pHEMA. Furthermore, various comonomers can be used in combination to alter the hydrophilicity, mechanical and swelling properties of the hydrogel (e.g. PEG, NVP, MAA). Non-limiting examples of polymers include 2-Hydroxyethyl methacrylate, polyacrylamide, N-vinylpyrrolidone, N,N-Dimethylacrylamide, poly(ethylene glycol) monomethacrylate (of varying molecular weights), diethylene glycol methacrylate, N-(2-hydroxypropyl)methacrylamide, glycerol monomethacrylate, 2,3-dihydroxypropyl methacrylate and combinations thereof. Non-limiting examples of cross-linkers include tetraethylene glycol dimethacrylate, poly(ethylene glycol) (n) diacrylate (of varying molecular weights), ethoxylated trimethylolpropane triacrylate, bisacrylamide and combinations thereof. Non-limiting examples of initiators include Irgacure Series (UV), Azobisisobutyronitrile (AIBN) (thermal), Ammonium Persulfate (APS) (thermal).

In a specific embodiment, the polymer is a luminescent hydrogel prepared by co-polymerization of HEMA and compound of Formula 1. In a preferred embodiment, the hydrogel is prepared by co-polymerization of various molar amounts of compound of Formula 2 mixed with 2-hydroxyethyl methacrylate (HEMA) monomer, tetraethylene glycol dimethacrylate (TEGDMA) crosslinker, Irgacure 651 initiator, water and co-solvent, followed by UV-initiated polymerization. In another embodiment, the polymer contains 1 mM final concentration of Compound of Formula 1. In a specific embodiment, the polymer is an oxygen sensing poly(2-hydroxyethyl methacrylate) (pHEMA) scaffold prepared by co-polymerization of HEMA (2-hydroxyehtyl methacrylate) (50 Wt %), TEGDMA (triethyleneglycoldimethacrylate) (1 Wt %1), ethylene glycol (20 Wt %), water (25.5 Wt %), the photoinitiator Irgacure 651 (0.5% vol/vol) and 3% of Compound 2.

The polymer of the present invention may be degradable, either by the body (biodegradable) or by the application of an external initiator to start or speed up the degradation process (e.g. UV, ultrasonics, radio frequency, temperature, or other exogenous sources to initiate degradation.). For example, the polymer may be biodegradable or bioresorbable or may comprised any biodegradable or bioresorbable segments, including but not limited to degradable forms of alginates, poly(lactic acid), poly(vinyl alcohol), polyanhydrides, poly(glycolic acid), microporous polyesters, microporous polyethers and cross-linked collagen. One specific example is UV-photopolymerization of poly(ethylene glycol)-diacrylate and acrylated protease-degradable peptides and VEGF as described by Phelps, et al (2010) *Proc. Nat'l. Acad Sci. USA* 107(8):3323-3328.

In one embodiment, polymers provided herein are biocompatible. In another aspect of the invention, the polymers are biodegradable. Degradable hydrogels can be synthesized using Atom Transfer Radical Polymerization (ATRP) through co-polymerization of the HEMA with polymerizable luminescent dyes of the present invention. Porous sensor scaffolds, based on non-degradable and degradable oxygen-sensing hydrogels, can be generated by using a sphere-templating fabrication technique. Degradable and non-degradable HEMA reagents and polymerizable dye will be polymerized over templating microspheres, which are subsequently dissolved away with solvent to generate desirable non-degradable and degradable scaffolds. Briefly, using controlled ATRP, HEMA will be polymerized in the presence of bi-functional degradable PCL-based ATRP initiator and cross-linker. In this synthesis scheme, pHEMA chains grow at the same rate from both sides of degradable initiator, resulting in degradation products with a MW that is half that of the parent polymer. By controlling the MW of the parent polymer and the PEG and PCL units in the initiator and/or crosslinker, the degradation rate of the polymers can be varied. Limiting the MW of the parent polymer to 10 kDa results in degradation products that can be cleared by the body and an increased degradation rate while still preserving the hydrogel's mechanical strength.

In certain embodiments the polymers provided herein are stimuli-responsive, e.g., temperature or pH-sensitive polymers. One non-limiting example of such a stimuli-responsive polymer is a temperature-sensitive polymer derived from co-polymerization of NIPAM. Such polymers are useful for implantation of the sensor comprising said polymers in a desired location within tissue by first dissolving the polymer in a suitable for injection media at a lower than body temperature and then injecting the resulting solution into the tissue and/or at desired location of the body. As the polymer is subjected to a higher (e.g., body) temperature, it precipitates in or near the site of the injection where monitoring of oxygen is required.

C. Sensors

In some embodiments, the polymer of the present invention is incorporated into a sensor useful for detection of an analyte. The detection of the analyte can be in vitro or in vivo. The remaining sentences of this paragraph describe how the word "polymer" is used in section titled "C. Sensors". The polymer may have the molecules of Formula 1 and/or Formula 2 covalently bound to the polymer backbone. The molecules of Formula 1 and/or Formula 2 maybe attached to (e.g. via a covalent bond or other means) or contained within nanoparticle carriers or microparticle carriers or other carriers that are attached to or contained within the polymer. Such carriers may be covalently bound to the polymer backbone. The word polymer can be used interchangeably with the word sensor.

In one non-limiting example, the polymer is incorporated into an oxygen-sensing wound dressing that can be used to monitor the process of wound healing, e.g. to constantly and non-invasively assess one of the critical factors of healing (i.e. oxygenation).

In another embodiment, the polymer is incorporated into a powder, which is used directly in the wound as a sensor for wound-healing monitoring. The sensor of the present invention can also be in the form of an injectable, implant, a mesh or sutures to be used in applications which benefit from monitoring of oxygenation of skin or the underlying tissue, including, but not limited to wound healing monitoring, skin closure, hernia repair, flap transfer surgeries, reconstructive surgery, and other plastic surgery applications. The sensor of the present invention can also be used for measurement for microcirculatory dysfunction and peripheral artery disease. Specifically in revascularization procedures or upon administration of drug, tissue oxygen may be directly monitored. The sensor of the present invention can also be used in oncology applications to determine the degree of hypoxia in a tissue or an organ. In one embodiment, the sensor is used to monitor tumor growth in animal, including but not limited to, mouse or rat models used in oncology pharmaceutical and diagnostic research and discovery, e.g., cancer therapy dosing or monitoring of tumor metabolism. The sensor of the present invention can also be used in monitoring the state of pulmonary function, for example in COPD and asthma disease states. In yet another embodiment, the sensor is used for exercise or training optimization, e.g., soldier and athlete performance or personal exercise programs. The sensor can also be in the form of an oxygen-sensing tattoo.

Yet in another embodiment, the sensors of the present invention are used in neuroscience monitoring applications, where currently there are no tools available for continuous monitoring of oxygen, for example, in subarachnoid hemorrhage monitoring.

In one embodiment, the sensor of the present invention is a solid material that could be in form of a slab, rod, cylinder, particle or powder. In a specific embodiment, the sensor is in the form of a rod. In another embodiment, the sensor is in the form of a cylinder.

In another embodiment, the polymer of the present invention is incorporated into a tissue-integrating scaffold to provide a tissue-integrating sensor (as described in the US patent application 2012/0265034, incorporated herein by reference). The sensors described herein typically comprise a tissue-integrating scaffold (also referred to as a matrix) material. Preferably, the tissue-integrating scaffold of the invention may be constructed with materials and/or microarchitecture such that the scaffold promotes tissue-integration and/or vascularization. For example, porous scaffolds provide tissue biomaterial anchoring and promote in-growth throughout the pores. The resulting "hallway" or "channel" pattern of tissue growth are healthy, space-filling masses that persist over time and promote host cell integration. Most or all of the pores of the biomaterials described herein are preferably interconnected (co-continuous). The co-continuous pore structure of the biomaterials promotes space-filling in-growth of cells in the implant, which in turn limits the foreign body response and leads to long-term (greater than one week and up to years) persistence of the implant's ability to act as a sensor. Alternative structures that provide tissue integrating scaffolds include fibers (e.g., 1 to 10 or more microns in diameter, such as 5, 6, 7, 8, 9, 10 or more microns), which may be arranged in non-random or random configuration. Tissue-integrating scaffolds (in any configuration) can also be formed by multiphoton polymerization techniques. Kaehr et al. (2008) *Proc. Nat'l. Acad Sci. USA* 105(26):8850-8854; Nielson et al. (2009) *Small* 1:120-125; Kasprzak, Doctoral Dissertation, Georgia Institute of Technology, May 2009.

The polymer of the invention, preferably in the form of a tissue-integrating scaffold, may comprise any material in combination with the compound of Formula 1 or Formula 2, including but not limited to synthetic polymers, naturally-occurring substances, or mixtures thereof. Exemplary synthetic polymers include, but are not limited to polyethylene glycol (PEG), 2-hydroxyethyl methacrylate (HEMA), silicone rubber, poly([epsilon]-caprolactone) dimethylacrylate, polysulfone, (poly)methy methacrylate (PMMA), soluble Teflon-AF, (poly) ethylenetetrapthalate (PET, Daeron), Nylon, polyvinyl alcohol, polyacrylamide, polyurethane, and mixtures thereof. Exemplary naturally-occurring materials include, but are not limited to, fibrous or globular proteins, complex carbohydrates, glycosaminoglycans, extracellular matrix, or mixtures thereof. Thus, the polymer scaffold may include collagens of all types, elastin, hyaluronic acid, alginic acid, desmin, versican, matricelluar proteins such as SPARC (osteonectin), osteopontin, thrombospondin 1 and 2, fibrin, fibronectin, vitronectin, albumin, chitosan etc. Natural polymers may be used as the scaffold or as an additive.

In certain embodiments, the polymer of the invention, preferably in the form of a tissue-integrating scaffold, comprises a hydrogel. For example, the polymer may comprise a hydrogel, for example by reacting hydroxyethyl methacrylate (HEMA), poly (hydroxyethyl methacrylate), pHEMA. Furthermore, various comonomers can be used in combination to alter the hydrophilicity, mechanical and swelling properties of the hydrogel (e.g. PEG, NVP, MAA). Non-limiting examples of polymers include 2-hydroxyethyl methacrylate, polyacrylamide, N-vinylpyrrolidone, N,N-dimethylacrylamide, poly(ethylene glycol) monomethacrylate (of varying molecular weights), diethylene glycol methacrylate, N-(2-hydroxypropyl)methacrylamide, glycerol monomethacrylate, 2,3-dihydroxypropyl methacrylate and combinations thereof. Non-limiting examples of cross-linkers include tetraethylene glycol dimethacrylate, poly(ethylene glycol) (n) diacrylate (of varying molecular weights), ethoxylated trimethylolpropane triacrylate, bisacrylamide and combinations thereof. Non-limiting examples of initiators include irgacure Series (UV), Azobisisobutyronitrile (AIBN) (thermal), Ammonium Persulfate (APS) (thermal).

The polymer of the invention, preferably in the form of a tissue-integrating scaffold, may be a sphere-templated hydrogel, for instance an inverse colloid crystal, for example as described in U.S. Patent Publication No. 2008/0075752 to Ratner, et al. or other tissue integrating materials.

The polymer of the invention, preferably in the form of a tissue-integrating scaffold, may be degradable, either by the body (biodegradable) or by the application of an external initiator to start or speed up the degradation process (e.g. UV, ultrasonics, radio frequency, or other exogenous sources to initiate degradation.). For example, the polymer may be comprised of any biodegradable or bioresorbable polymers, including but not limited to degradable forms of alginates, poly(lactic acid), poly(vinyl alcohol), polyanhydrides, poly (glycolic acid), microporous polyesters, microporous polyethers and cross-linked collagen. One specific example is UV-photopolymerization of poly(ethylene glycol)-diacrylate and acrylated protease-degradable peptides and VEGF as described by Phelps, et al (2010) *Proc. Nat'l. Acad. Sci. USA* 107(8):3323-3328.

Other specific examples are polymers described by Kloxin et al (2009) *Science* 324:59-63 and U.S. Pat. No. 6,013,122 whose degradation is controlled through exposure to exogenous energy forms, as well as by Alexeev et al. (2003) *Anal. Chem.* 75:2316-2323; Badylak et al. (2008) *Seminars in Immunology* 20:109-116; Bridges et al. (2010) 94(1):252-258; Isenhath et al. (2007) *Research* 83A:915-922; Marshall et al. (2004) *Polymer Preprints, American Chemical Society, Division of Polymer Chemistry* 45:100-101; Phelps et al. (2010) *Proc Nat'l Acad Sci USA.* 107(8): 3323-8; Ostendorf and Chichkov (2006) *Two Photon Polymerization: A New Approach to MicroMachining, Photonics Spectra*; Ozdemir et al. (2005) *Experimental and Clinical Research. Plast. Reconstr. Surg.* 115:183; U.S. Patent Publication No. 20080075752; Sanders et al. (2003) *Journal of Biomedical Materials Research* Part A 67A(4):1181-1187; Sanders et al. (2002) *Journal of Biomedical Materials Research* 62(2):222-227; Sanders et al. (2003) *Journal of Biomedical Materials Research* 65(4):462-467; Sanders et al. (2005) *Biomaterials* 26:813-818; Sanders et al. (2005) *Journal of Biomedical Materials Research Part A* 72(3): 335-342; Sanders (2003) *Journal of Biomedical Materials Research* 67(4):1412-1416; Sanders et al. (2000) *Journal of Biomedical Materials Research* 52(1):231-237; and Young Min Ju et al. (2008) *J Biomed Mater Res* 87A:136-146.

In certain embodiments, the polymer of the invention, preferably in the form of a tissue-integrating scaffold, is constructed such that tissue response modifiers are released from the scaffold material to promote or enhance tissue-integration and vascularization.

In addition, the polymer of the invention, preferably in the form of a tissue-integrating scaffold, may be constructed such that it has conduits, pores or pockets that are hollow or filled with degradable, angiogenic, or other substances (e.g. stem cells). As noted above, once in the body, the biodegradation of the material filling the conduits, pores or pockets, creates space for tissue, including capillaries to integrate with the material. The degradable material that initially fills the conduits, pores, or pockets may enhance vessel growth or tissue growth within the scaffold. This architecture promotes new vessel formation and maintains healthy viable tissue within and around the implant.

The polymer of the invention, preferably in the form of a tissue-integrating scaffold, may be constructed such that it is permeable to analytes of interest (e.g., oxygen can diffuse into a tissue-integrating hydrogel scaffold and reach the sensing moieties that are embedded within the hydrogel matrix).

The polymer of the invention, preferably in the form of a tissue-integrating scaffold, can be of any suitable form, including, but not limited to block-like (or any thickness), cube-like, disk-shaped, cylindrical, oval, round, random or non-random configurations of fibers and the like. In certain embodiments, the sensor comprises one or more fibers, which may be organized in a non-random fashion (e.g., grid, layered grid, etc.) or in a random fashion.

The polymer of the invention, preferably in the form of a tissue-integrating scaffold, described herein are typically combined with (or made up of) sensing moieties that detect one or more analytes. In one embodiment, the sensing moiety is the residue of compound of Formula 1 and/or 2 incorporated into the tissue-integrating scaffold.

In another embodiment, the polymer of the invention, preferably in the form of a tissue-integrating scaffold, comprises, in addition to the residue of compound of Formula 1 and/or Formula 2, a second sensing moiety that produces or consumes oxygen, e.g., an oxidase, and the residue of compound of Formula 1 and/or Formula 2 is used to detect the change in the oxygen concentration generated by the second sensing moiety. The second sensing moiety can comprise an enzyme, for example glucose oxidase (GOx), which is specific for the substrate glucose. The reaction of glucose via enzymatic interaction with glucose oxidase causes oxygen to be proportionally consumed and converted to $H_2O_2$. The reduction of $O_2$ in the vicinity of the enzyme can be measured by using an $O_2$-sensitive fluorescent dye, such as the molecules of Formula 1 and Formula 2. These dye molecules are quenched in the presence of $O_2$, so the reduction of $O_2$ by the action of GOx, causes an increase in fluorescence. The amount of fluorescence emitted from the $O_2$ calibration moieties is thus proportional to the concentration of glucose in the sensor. Oxidases besides glucose oxidase for detection of other analytes besides glucose may include billirubin oxidase, ethanol oxidase, lactate oxidase, pyruvate oxidase, histamine oxidase or other oxidase to provide specificity to other analytes of interest.

The concentration of $O_2$ in the tissue can also vary physiologically, thereby changing or limiting the reaction of the oxide enzyme in the sensing moieties. Therefore, the $O_2$ concentration in the sensor can be measured independent of the oxidase target concentration. This may be accomplished through physical separation on some nanometer, micro on mm scale of $O_2$ reference moieties from the enzyme-$O_2$ detection moieties to avoid cross talk. Such a reference measurement of $O_2$ would allow corrections to be made to the glucose-specific signal from the oxidase sensing moieties.

In another embodiment, the polymer of the invention, preferably in the form of a tissue-integrating scaffold, may be a multi-analyte sensor where oxygen is one of two or more analytes detected and reported. In this embodiment, the polymer comprises a residue of compound of Formula 1 and/or Formula 2 for detection of oxygen, and a second sensing moiety for detection of another substance. Non-limiting examples of analytes that may be detected by the sensing moieties include oxygen, reactive oxygen species, glucose, lactate, pyruvate, cortisol, creatinine, urea, sodium, magnesium, calcium, potassium, vasopressin, hormones (e.g., Luteinizing hormone), pH, cytokines, chemokines, eicosanoids, insulin, leptins, small molecule drugs, ethanol, myoglobin, nucleic acids (RNAs, DNAs), fragments, polypeptides, single amino acids and the like.

In another embodiment, the polymer of the invention, preferably in the form of a tissue-integrating scaffold, may be a sensor where the oxygen signal, as detected by Formula 1 and/or Formula 2, is used as a reference to correct or calibrate the signal for one or more other analytes. The oxygen signal may or may not be reported. It may be used only in internal algorithms to calibrate or correct the signal of the other analyte. The use of the oxygen signal as a reference in this embodiment helps to overcome physiological fluctuations, which may alter the analyte availability at the site of the sensor (e.g. blood flow variations).

In still further embodiments, the sensing moieties, in addition to the residue of compound of Formula 1 and/or Formula 2 comprise a second luminescent analyte sensing moiety, and the residue of the compound of Formula 1 and/or Formula 2 is used as a reference molecule. The non-oxygen sensing moieties may utilize analyte-specific moieties such as competitive binding assays (e.g. a ligand receptor moiety and an analyte analogue moiety such as Concanavalin A and dextran), reversible luminescent binding molecules (e.g. boronic acid based sensing chemistry for glucose detection), binding proteins such as glucose binding proteins. To measure an analyte such as glucose in the tissue, the polymer is illuminated from a patch reader on top of the skin above the implant with 650 nm light at desired intervals over the long-term life of the implant (e.g., every 5-60 minutes over a period of 90 days or more). The amount of luminescent signal (e.g., from a molecule such as Alexafluor 647) detected is proportional to the concentration of analyte (e.g. glucose) in the tissue. The amount of luminescent signal (e.g. from Formula 1 or Formula 2 molecule) detected is proportional to the concentration of $O_2$ in the tissue. The concentration of $O_2$ in the tissue is indicative of acute and or chronic physiological changes around the sensor, and may be used to correct or adjust the glucose signal or other analyte signal through a proportionality algorithm.

In another embodiment, internal reference control materials can be employed that facilitate correcting for tissue optical variation. The tissue-integrating implanted biosensor typically resides 3-4 mm under the surface of the scan. It is well known that in skin excitation light and emitted fluorescent light in the near infrared range are highly scattered as the light traverses the tissue between the reader patch and the implant. The extent of absorption and scattering is affected by physical properties such as temperature or by tissue composition, including but not limited to variations in blood perfusion, hydration, and melanin concentration. Skin variations can occur between users or between different time points for a single patient, and these variations can affect the fluorescence excitation and emissions signals causing in accurate signals for the analyte-specific signal. Accordingly, a separate fluorescence molecule with emission spectra distinguishable from the analyte-specific fluorescence can be immobilized into the scaffold. The fluorescence from the molecule can be measured separately from the analyte-specific fluorescence to measure a signal that informs about variations in tissue composition. The dye selected is based on having a similar response to tissue variations as the analyte-specific dye. Formula 1 or Formula 2 may have the oxygen sensing capabilities greatly reduced or eliminated, for example, by incorporation in a non-oxygen diffusive environment such as embedding in highly crosslinked PAN or inside a silica shell. In this format, the dye molecules of this invention may serve as the stable internal reference control materials described above.

Tissue-integrating sensors comprised of one or more cylindrical shaped elements (e.g., fibers) eliminate or greatly reduce the foreign body response as compared to currently available implants. Moreover, the average diffusion distances from the capillary supply to all parts of the sensing media are comparable to native tissue, unlike other known sensors.

It will be apparent that the overall dimensions of the sensing media (implantable sensor) will vary according to the subject and/or the analyte(s) to be measured. Typically, the implant will be between about 0.001 mm to 2 mm in thickness (or any value therebetween) and between 1 mm and 1 cm in diameter (or an equivalent cross sectional area of a non-circular shape, for example length/width) and 15 mm in length or less, for example, a disk shaped sensor that is 2 mm or less thick and 10 mm or less in diameter. In certain embodiments, the approximate sensor size is approximately 100-1000 microns in diameter and has the length of between 0.25 mm and 10 mm. The size of the tissue-integrating sensing media in disk form is typically 2 mm or less thick and 10 mm or less in diameter.

Another aspect of the present invention is a tissue-integrating biosensor system for semi-continuous, continuous and/or long-term use within a mammalian body.

One advantageous property of the polymers of the present invention is their stability. In one aspect of the invention, the sensor is stable in a mammalian tissue for a long period of time, e.g., longer than a week, longer than a month, longer than 6 months. In one exemplary embodiment, as shown by the FIG. 2, the sensor is stable and produces a stable signal when implanted into the rat skin for 170 days.

EXAMPLES

NMR spectroscopic data were recorded on a 300 MHz instrument at room temperature. NMR spectra were calibrated to the solvent signals of deuterated DMSO-d6 or CDCl3. The following abbreviations are used to indicate the signal multiplicity: s (singlet), d (doublet), t (triplet), q (quartet), br (broad), m (multiplet). Analytical HPLC-MS data were recorded on a HPLC system with a C18 reverse column coupled to an electrospray ionization (ESI) spectrometer. 2-Aminoethyl methacrylate hydrochloride and tetraethylene glycol dimethacrylate were purchased from Polysciences, Inc. All other chemicals were purchased from Sigma Aldrich.

Example 1: Synthesis of a Polymerizable Near-IR Luminescent Dye

Scheme 1 describes the synthesis of one exemplary near-IR luminescent dye, Compound 2 (also referred to as Pd-BP):

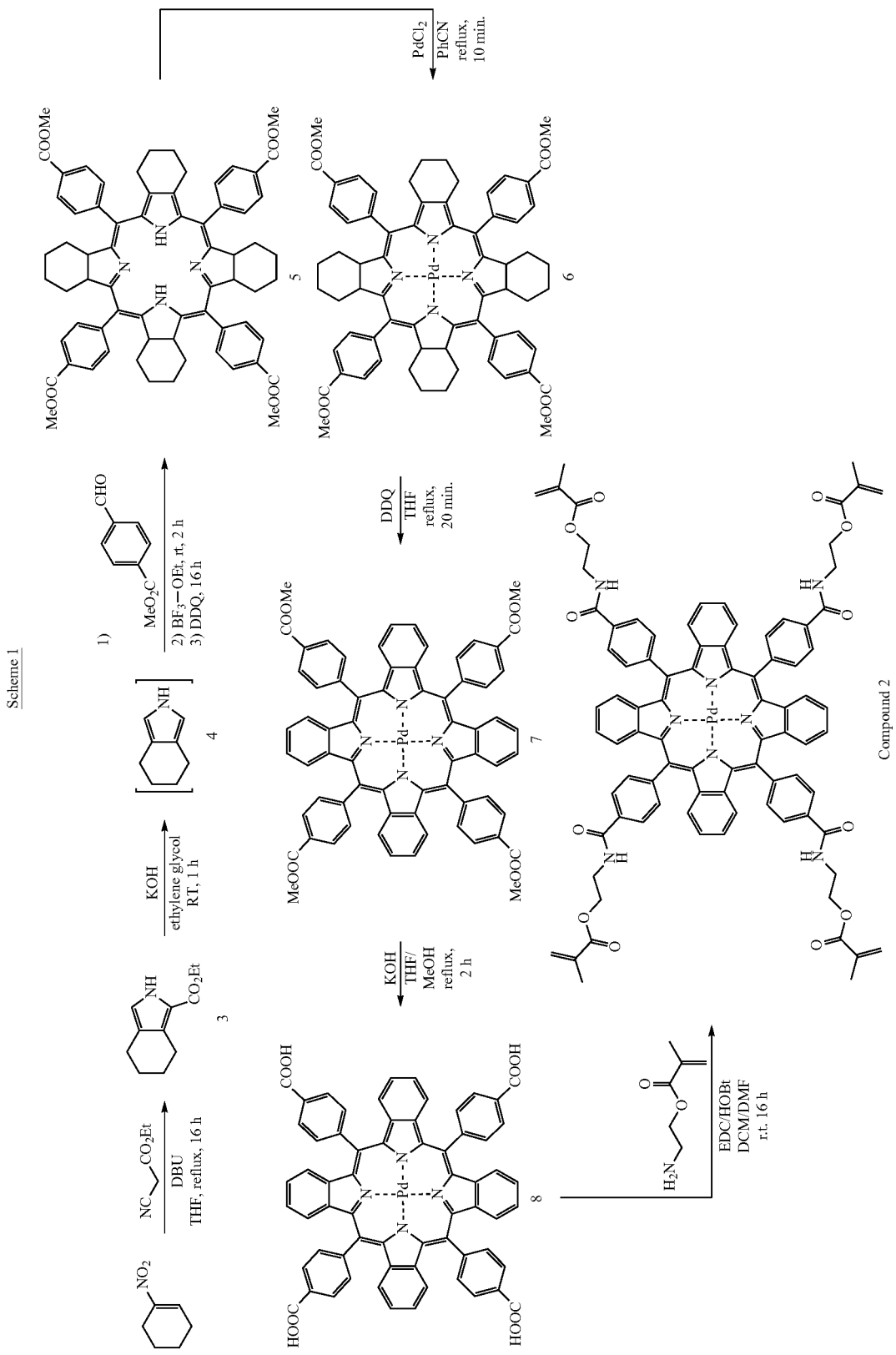

Compound 3 was prepared as described in Niedermair et al, J. Inorg. Chem., 2010, 49, p. 9333. Briefly, to 90 mL of anhydrous THF was added 1-nitrocyclohexenene (2.66 mL), ethyl isocyanoacetonitrile (2.6 mL), and DBU (3.53 mL). The reaction was refluxed at 70° C. under argon for 18 hours. Brown precipitate formed as soon as heating began. THF was evaporated, the residue was dissolved in methylene chloride, and the product was purified by flash chromatography on silica gel in methylene chloride. Product-containing fractions were evaporated under vacuum to remove most of the solvent, and to the residual solution hexanes were added to facilitate crystallization of the product. After 48 hr at 4° C., the precipitate was collected to by filtration to yield 2 g of the product as fine yellow needles. The mother liquor was partially evaporated to yield additional 1.4 g of the product; 75% total yield.

Compound 5:

Compound 3 (1.40 g, 7.2 mmol) was suspended in 30 mL of anhydrous ethylene glycol, and KOH pellets (0.73 g, 13.0 mmol) were added to the solution. The mixture was refluxed under argon for 1 hr. The resulting clear brown solution was cooled to 0° C., and 100 mL of dichloromethane was added to the solution. Dichloromethane layer was separated, washed with water (2×100 mL), and brine (2×100 mL) and dried over anhydrous sodium sulfate. The product was purified by flash chromatography on silica gel in dichloromethane. Fractions containing the fast-running component were pooled and diluted with dichloromethane to 1000 mL. To the resulting solution was added methyl-4-formyl benzoate, under argon, the solution was stirred at room temperature for 10 min, and $BF_3 \cdot OEt_2$ (0.19 mL, 1.3 mmol) was added. The mixture was stirred for 2 hr, then 1.73 g (7.6 mmol) of DDQ was added, and the mixture was allowed to stir overnight. The mixture was washed sequentially with 10% aq. $Na_2CO_3$, 1M HCl, and brine, then dried over anhydrous sodium sulfate. After purification by silica gel chromatography using stepwise gradient of MeOH in dichloromethane (0-2%), 430 mg (24%) of the product as green powder.

Compound 6:

Compound 5 as a free base (0.43 g, 0.40 mmol) was dissolved in 50 mL of benzonitrile. To the solution, PdCl2 was added under argon, and the mixture was refluxed for 10 min. The color of the solution changed from green to red. The mixture was cooled to room temperature, diluted with 200 mL of dichloromethane, and filtered through Celite. Dichloromethane was evaporated under vacuum, and benzonitrile was distilled off. The product was purified by flash chromatography on silica gel in dichloromethane, and the final purification was achieved by flash chromatography on silica gel in hexanes:ethyl acetate (1:1) to yield 0.109 mg (60%) of the product as a red powder.

Compound 7:

Compound 6 (0.105 g, 0.09 mmol) was dissolved in 20 mL of anhydrous THF, and DDQ (0.327 g, 1.44 mmol) was added to the solution. The mixture was refluxed for 20 min, and the reaction was stopped when no starting material was detected in the mixture by TLC. THF was removed under vacuum, the residue was diluted with dichloromethane and washed sequentially with 10% $Na_2SO_4$, water, and brine.

Compound 8:

The ester 7 was hydrolyzed as described in Finikova et al., J. Phys. Chem., 2007, 111, p. 6977. Briefly, 0.074 g (0.064 mmol) of Compound 7 were dissolved in 110 mL of THF. To the solution, MeOH (10 mL) was added, followed by a solution of 0.573 g of KOH in 2 mL of MeOH. Green precipitate formed in the solution, and the solution became almost colorless. The precipitate was collected by centrifugation and dissolved in 10 mL of water. The solution was acidified with 0.2 mL of concentrated HCl, and the resulting precipitate was collected by centrifugation. Yield: 0.070 g (86%).

Compound 2:

Compound 8, 30 (70 mg, 63.9 µmol) in DMF (10 mL) and $CH_2Cl_2$ (10 mL) at 0° C. was added 1-hydroxybenzotriazole hydrate (43.17 mg, 0.32 mmol), N-(3-dimethylaminopropyl)-N'-ethylcarbodiimide hydrochloride (61.25 mg, 0.32 mmol), and triethylamine (90 µL, 0.64 mmol). After 20 min., 2-aminoethyl methacrylate hydrochloride (53.23 mg, 0.3195 mmol) was added, and the reaction was stirred for 16 h at room temperature. The $CH_2Cl_2$ was evaporated under reduced pressure, and ethyl acetate/hexanes mixture was added to precipitate the crude product from residual DMF. The solvent was decanted, and the precipitated residue was dissolved in $CH_2Cl_2$, washed sequentially with sat. $NaHCO_3$ and brine, dried over $Na_2SO_4$, filtered, and concentrated in vacuo. The crude product was purified by flash chromatography on silica gel (gradient of 0-4% methanol in $CH_2Cl_2$) to yield Compound 2 as a green powder (16 mg, 16% yield). 1H NMR (300 MHz, $CDCl_3$) δ 8.40 (d, J=8.1 Hz, 8H), 8.32 (d, J=8.1 Hz, 8H), 7.22 (br s, 8H), 7.10 (br s, 811), 6.28 (s, 4H), 5.71 (s, 4H), 4.61 (t, J=5.4 Hz, 8H), 4.03 (q, J=5.1 Hz, 8H), 2.06 (s, 12H). LC-MS (ESI): calcd for $C_{88}H_{73}N_8O_{12}Pd$: 1539.4403 [M+H]+, found 1539.4405 [M+H]+, $R_t$=11.8 min.

Compound 9 was synthesized analogously to Compound 2 by reacting commercially available tetracarboxyphenyl porphyrin with ainoethyl methacrylate in the presence of HOBt and EDC as shown in Scheme 2:

Scheme 2

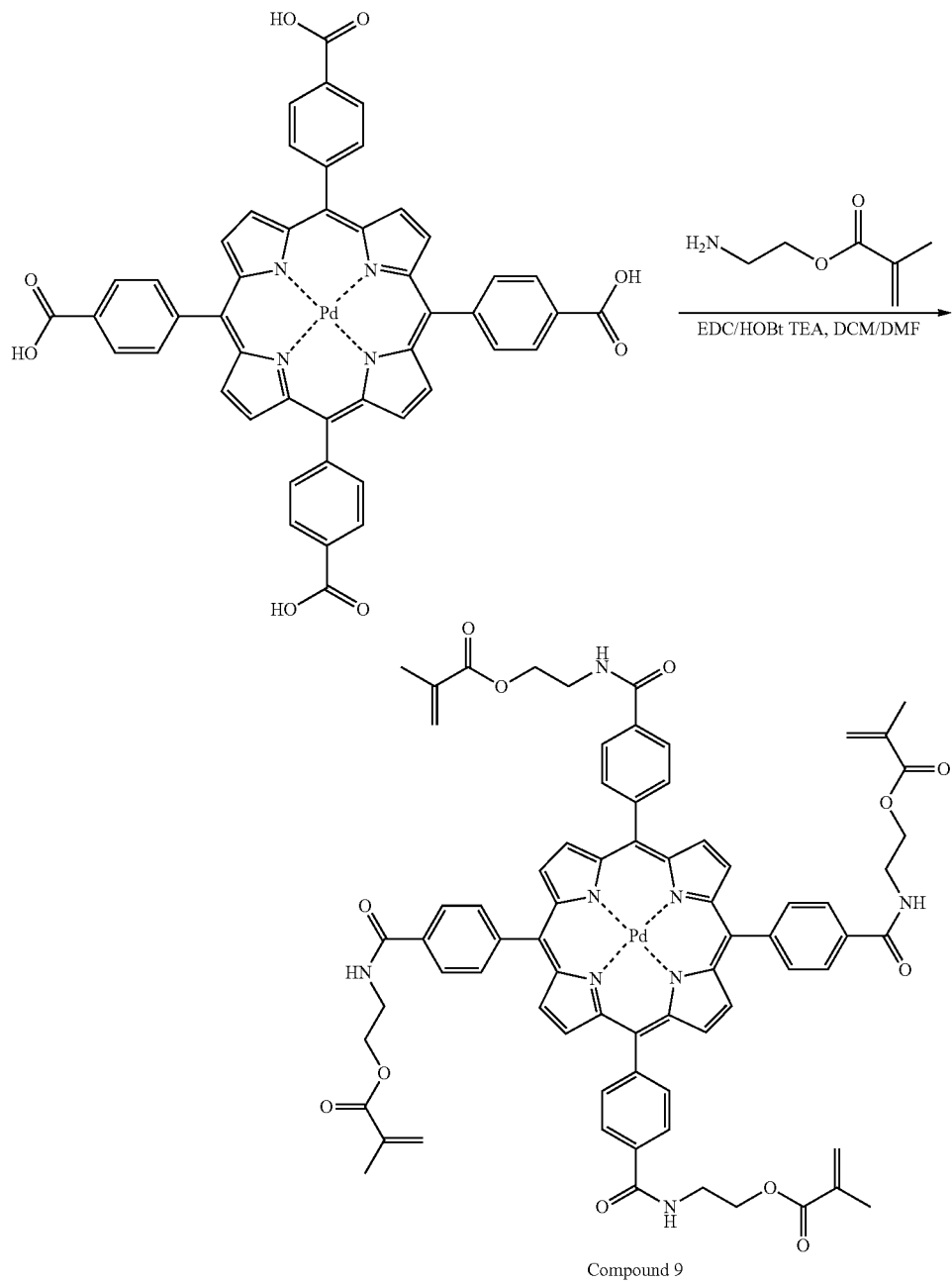

Compound 9

Example 2: Production of an Oxygen Sensing Media with Oxygen Sensitive Luminescent Dye Immobilized in a Tissue-Integrating Hydrogel Scaffold The following describes one method for making a tissue-integrating sensor as described herein. This method involves the use of non-crosslinked PMMA templating microspheres and pHEMA as the scaffold material. The PMMA microsphere template was prepared using monodispersed PMMA spheres (20-100 um, preferably 80 um) and placing the template beads between two glass slides with Teflon spacers. The sintering process included sonicating for at least 10 minutes (one or more times) to closely pack the beads. Following sonication, the template is heated to a sufficient temperature for a sufficient time to fuse the beads (typically, to 140-180° C. for 20-32 hours, for example, heat to approximately 177° C. for 24 hours). For each lot of the beads, the temperature and heating times are optimized.

The general preparation of an oxygen sensing poly(2-hydroxyethyl methacrylate) (pHEMA) scaffold was performed as follows: HEMA (2-hydroxyehtyl methacrylate) (50 Wt %), TEGDMA (triethyleneglycol-dimethacrylate) (1 Wt %1), ethylene glycol (20 Wt %), water (25.5 Wt %), the photoinitiator Irgacure 651 (0.5% vol/vol) and 3% of Palladium-tetramethacrylate-benzoporphyrin (Compound 2, polymerizable $O_2$ sensitive dye) were mixed, yielding a final concentration of 1 mM Compound 2 in the polymer precursor solution. Polymer, solvents and sensing reagents were mixed to achieve sufficiently high sensing chemistry concentration to measurably detect a change in signal through tissue.

The pre-mixed monomer solution was filled into the PMMA mold. The solution was placed under vacuum to remove any bubbles and to completely infiltrate the PMMA-mold. Polymerization was initiated by exposing the mold to UV light (280-320 nm, 10-300 mW/cm2) for 5-10 minutes. Next, the PMMA microspheres were dissolved out of the resulting polymer by frequent exchange of dichloromethane or other solvent system for 24-48 hours using a Soxhlet extractor by manual volume changes.

The following describes preparation of the rod hydrogel sensors. 100 µL of a 10 mM solution of Compound 2 in DMSO, was added to a polymer precursor solution [2-hydroxyethyl methacrylate (0.5 mL, 4.1 mmol), tetraethyleneglycol dimethacrylate (10 µL, 34 µmol), ethylene glycol (0.2 mL), water (185 µL) and 2,2-dimethoxy-2-phenylacetophenone (5 mg, 2 µmol)], yielding a final concentration of 1 mM Compound 2. The dye and polymer precursor mixture was injected into a poly(methyl methacrylate) (PMMA) bead-containing glass mold, as previously described by Marshall, A. J. et al. (Biomaterials with Tightly Controlled Pore Size that Promote Vascular In-Growth. ACS Polymer Preprints 45, 100-101 (2004)). The mold was placed under vacuum to remove any bubbles and to ensure complete filling. Polymerization was initiated by exposing the mold to UV light (280-320 nm) using a Dymax 2000-EC Flood Curing System equipped with a 400 Watt Mercury bulb for 2 minutes per side at a distance of approximately 6". The glass plates were removed and the hydrogel was soaked in 50 mL of $CH_2Cl_2$ (exchanged twice) with shaking for 24 hours to extract out the PMMA beads. The hydrogel was transferred into water and placed under vacuum for 5 minutes to fully hydrate the porous scaffold. For implantation, the hydrogels were cut into rods (10 mm in length with a 750 µm×750 m cross-section), disinfected by exposure to 70% ethanol, and then stored in sterile pH 7.4 PBS at 4° C. before use. Non-porous (i.e., solid) hydrogel sensors were prepared analogously but without the use of templating beads.

Figure 5:
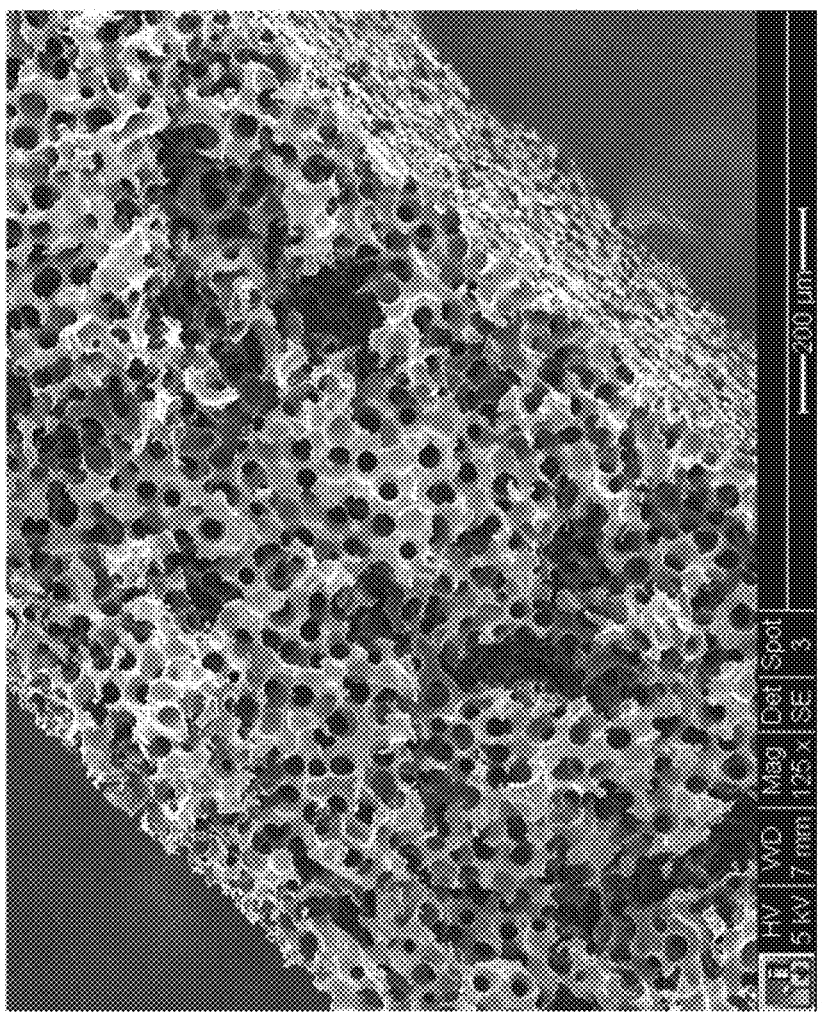
FIG. 5 shows a SEM image of tissue-integrating porous hydrogel scaffold.

Hydrogels comprising Glucose oxidase (GOx) were also prepared as described above except GOx was also included in the polymerization mixture used to prepare the scaffold (FIG. 5).

Example 3: Determination of Excitation and Emission Wavelengths of Compound 2 Incorporated into a Hydrogel The absorption and emission spectra of the dye-containing hydrogels generated in Example 2 were measured in pH 7.4 PBS at ambient atmosphere using a fluorescence plate reader (FIG. 1). The absorption spectra contained a Soret band at 445 nm and a Q band at 633 nm. Excitation at 633 nm gave an emission peak at 805 nm, thus confirming that Pd-BP (Compound 2) exhibits both absorption and emission in the NIR.

Example 4: Determination of Optimal Dye Concentration in Hydrogel

To determine the minimum dye concentration required to achieve a maximum intensity signal, a series of pHEMA hydrogels containing various concentrations of Pd-BP (Compound 2) were made. Solid and porous pHEMA hydrogels containing covalently-bound Pd-BP (Compound 2) at 0.01, 0.1, 1, 2, and 3 mM dye concentrations were prepared. All gels were ~1 mm thick; porous gels contained an average pore size of ~70 µm. While in pH 7.4 PBS in ambient air, the fluorescence emission of each gel was measured at 805 nm (633 nm excitation) using a fluorescence plate reader. From these data, the optimal dye concentration was determined to be 1 mM, since signal saturation was observed at higher concentrations.

Example 5: Characterization of Photobleaching of NIR Benzoporphyrin

Hydrogels containing covalently-bound Compound 2 were used in photobleaching studies to determine the photostability of Compounds 2 and 9. The hydrogels were tested in a custom-built flow-through system intended to simulate physiological conditions (pH 7.4 PBS, 37° C., 21% $O_2$) while being illuminated by LED. The excitation light was directly delivered to the bottom face of the gel samples via 1 mm diameter fiber optic cables. Hydrogels containing Compound 9 were excited with a 525 nm LED source (power=127 mW/cm$^2$) having a pulse duration (LED "on time") of 2 seconds and a pulse period of 5 seconds to achieve an overall duty cycle of 40%, while Compound 2 containing hydrogels were excited with a 630 nm LED source (power=143 mW/cm$^2$) with the same duty cycle. The experiment was run for 15 continuous hours under these conditions. However, less than 5% change in the lifetime signal of Compound 2 was observed. The resulting data from this experiment is used to estimate the expected degree and rate of photobleaching which can occur during long-term in vivo use.

Figure 6:
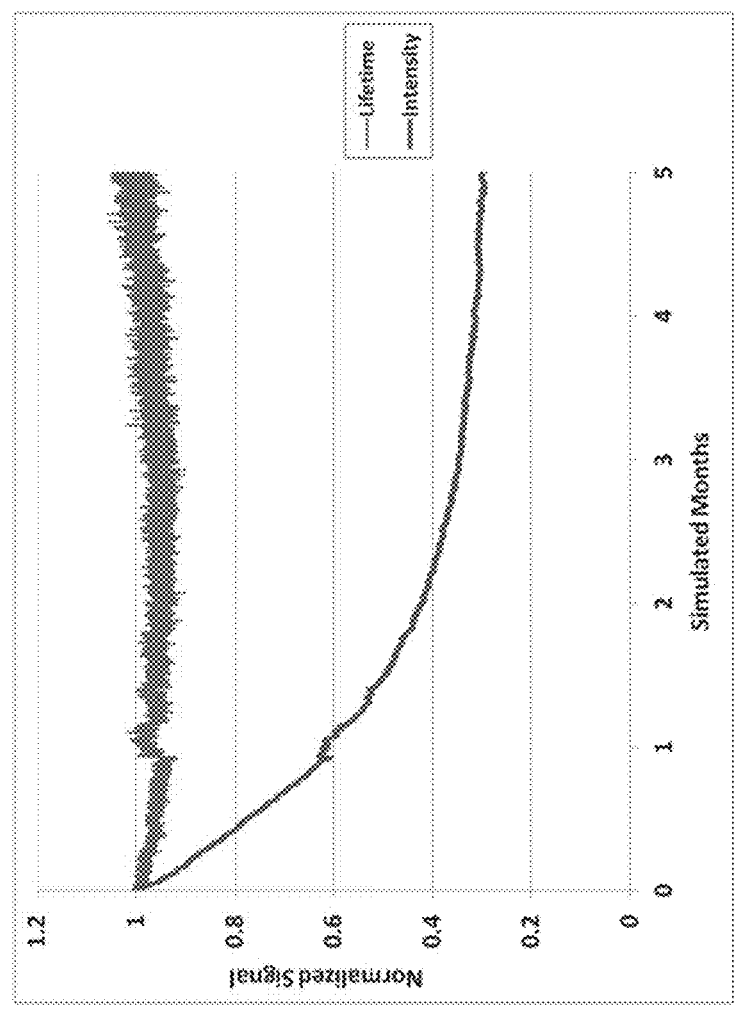
FIG. 6 demonstrates determination of photostability Pd-BP. Gels in PBS (pH 7.4, 37° C.) were illuminated using a 525 nm LED at a 40% duty cycle. Both lifetime signal remains constant.
Figure 7A:
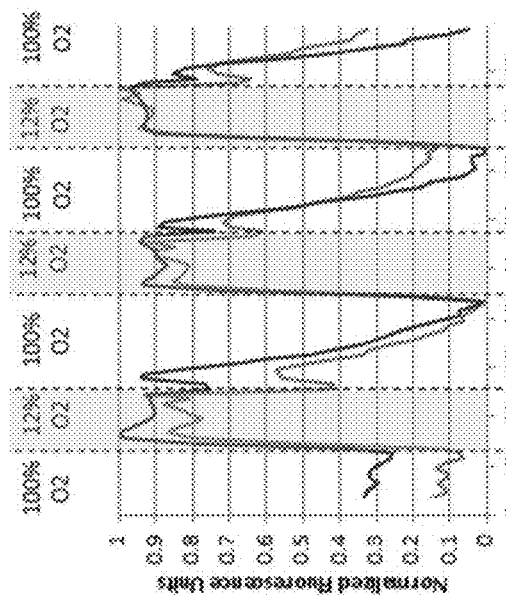
FIG. 7A depicts that the response of the porous, tissue-integrated sensors is rapid (~30 seconds). The solid sensors are rod-shaped and material composition.
Figure 7B:
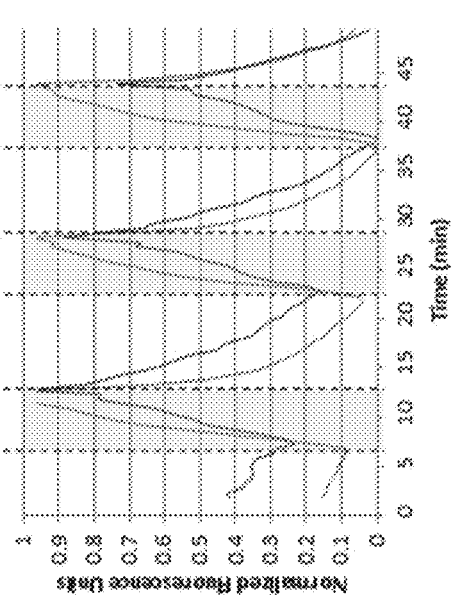
FIG. 7B depicts that the response of the solid sensor response is much slower (plateau not even reached after 5 minutes). The solid sensors are the same rod-shape and material composition as shown in FIG. 7A.

Gels containing the dye were extremely photostable when tested under simulated use conditions (FIG. 6). These data indicate that measurement of the lifetime signal is a preferable strategy to achieve long-term (5 months) stability in vivo. Photostability of the Pd-BP compound may be further improved using techniques elsewhere disclosed, e.g. changing the metal core, or fluorinating or perfluorinating the base compound.

Example 6: Implantation

A tissue integrating sensor produced in rods that are 300-500 um in diameter and 5 mm long are placed in a 19-23 Gauge insertion needle, trochar, modified biopsy device or other devices engineered for injection under the skin. The sensor is optionally dehydrated or compressed before insertion to allow for the use of a smaller insertion needle.

Figure 3:
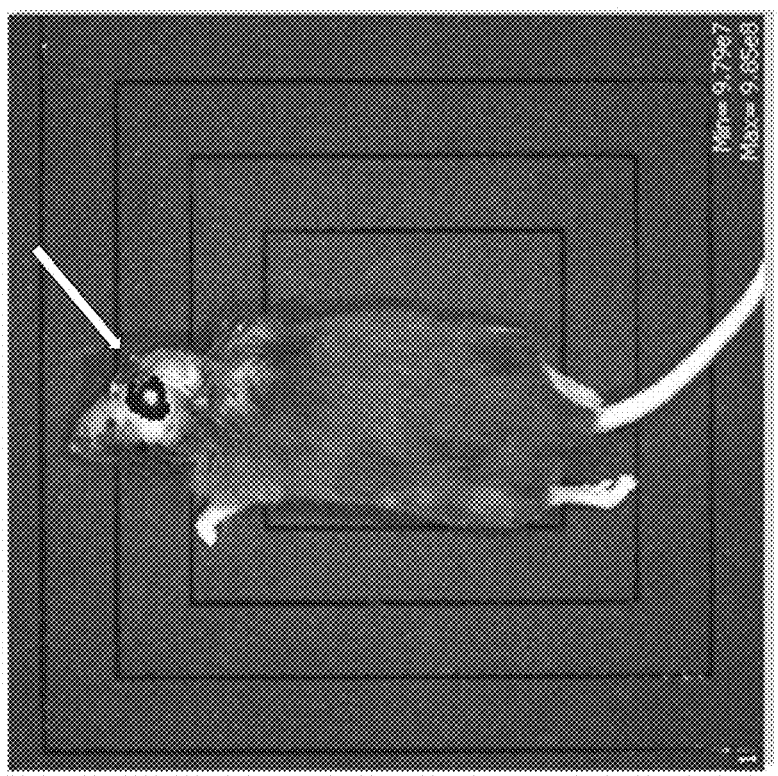
FIG. 3 depicts luminescence signal of pHEMA $O_2$ sensor implanted in a mouse brain.
Figure 4:
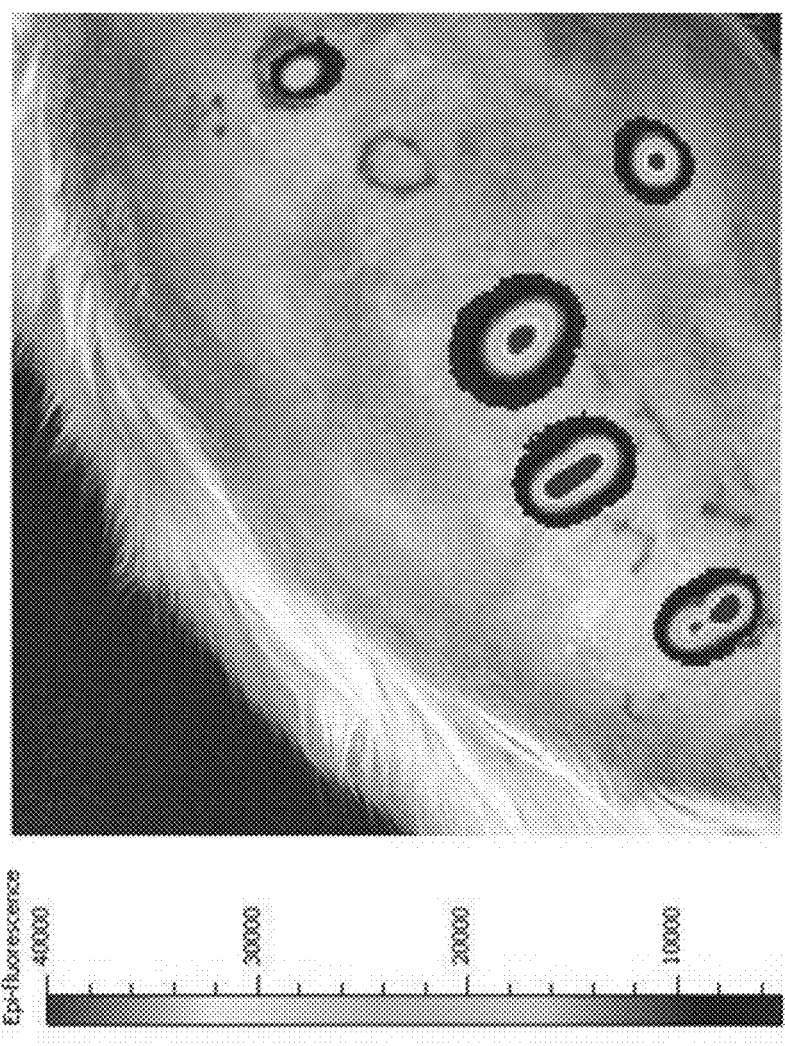
FIG. 4 depicts luminescence of oxygen sensors implanted in rat skin (170 days). Intensity varies as a function of implantation depth (data normalized to baseline fluorescence) and tissue oxygen concentration. Inhaled oxygen was modulated between 100% and 12% and images were collected every 30 s in a Caliper IVIS (Ex=640 nm, Em=800 nm). Regions of interest (ROIs) were drawn around the sensors and the data plotted versus time. Data is shown in FIG. 6.

Upon insertion, skin is pinched up so that the insertion needle is placed parallel to the surface of the skin up to 4 mm beneath the surface. Fluid or a reverse displacement plunger (or trochar) is used to leave the sensor in the tissue as the syringe is withdrawn. Insertion site may include any subcutaneous or dermal area, typically the abdomen, arm and thigh (FIG. 4). In research models, the dorsal skin, abdomen, hindlimb and brain (FIG. 3) have all been explored. The following describes an example of hydrogel implantation, in-vivo fluorescent imaging, and data analysis in a rat model.

Hydrogel Implantation and In Vivo Fluorescent Imaging.
Hydrogel sensors (n=3 to 4 porous and n=3 to 4 solid), were injected into the subcutaneous tissue of 12 adult male CD rats (Charles River Labs, 150-250 g) for 1 week, 4 weeks, or 170 days. Rats were anesthetized with 2-3% isoflurane (v/v in oxygen) during sensor injection. Porous and solid hydrogel rods (10 mm long, 750 µm×750 µm cross-section) were loaded into 18 gauge needles and then inserted into the dorsal subcutaneous space perpendicular to the midline. Sensors were ejected from the needle by inserting a stainless steel plunger through the cannula. Hydrogel sensors were implanted approximately 1.5 cm apart. Rats grew normally and showed no discomfort during the weeks following the sensor injection.

Oxygen sensors were fluorescently imaged once every 30 seconds in vivo with the IVIS Spectrum or Kinetic imaging system (Perkin Elmer, Waltham, Mass., USA). Rats were anesthetized at 2% isoflurane in 1.00 FIO2 for 30 minutes prior to imaging. During in vivo imaging, the FIO2 was at least twice modulated down to 0.12 (v/v balance N2) for 5-10 minutes and then returned to 1.00 for 10-15 minutes. The relative response (intensity) of each sensor was quantified by identifying regions of interest (ROIs) surrounding the sensors and measuring the average radiant efficiency in the ROI using the Living Image Software included with the IVIS System.

On the day of implantation, the Oxford Optronics Oxy-Lite system was used as a reference for tissue oxygenation. A needle-encased OxyLite probe was inserted subcutaneously in the dorsum of the rat on the day of sensor injection (DO) and was allowed 10-15 minutes for the signal to reach a steady-state before data collection as described by Braun, et. al. (Comparison of tumor and normal tissue oxygen tension measurements using OxyLite or microelectrodes in rodents. *Am J Physiol Heart Circ Physiol* 280, H2533-2544 (2001)).

Data Analysis and Statistical Tests.

The data for each sensor, as defined by the ROI, was normalized to the maximum and minimum average radiant efficiency and inverted to have a positive correlation between the fluorescence data and tissue oxygenation. This normalization ensured that data for every sensor for each separate experiment fell between 0 and 1, which were the maximum and minimum intensity of the sensor, respectively.

The sensors often did not reach a plateau during hypoxia testing because animal health concerns necessitated the short exposure times (5-10 min). Therefore, to calculate the response time of the sensors, the time to achieve 90% of the fluorescent intensity change (T90%) during either the 10 min hypoxic (FIO2=0.12) or the 15 min hyperoxic (FIO2=1.00) event was determined. The sensors were declared to have reached a steady state if there was less than 10% of the total change over the last 3 minutes of the FIO2 change event. Data was tested for statistical significance using the non-parametric Wilcoxon rank-sum test (p<0.05).

Histological Analysis.

Figure 11B:
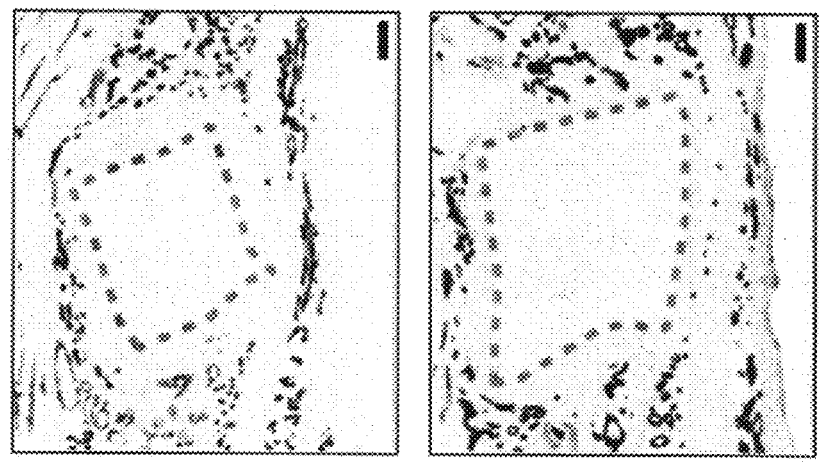
FIG. 11B shows fluorescent micrographs of solid sensors and surrounding tissue samples at 7 and 28 days after implantation.
Figure 11A:
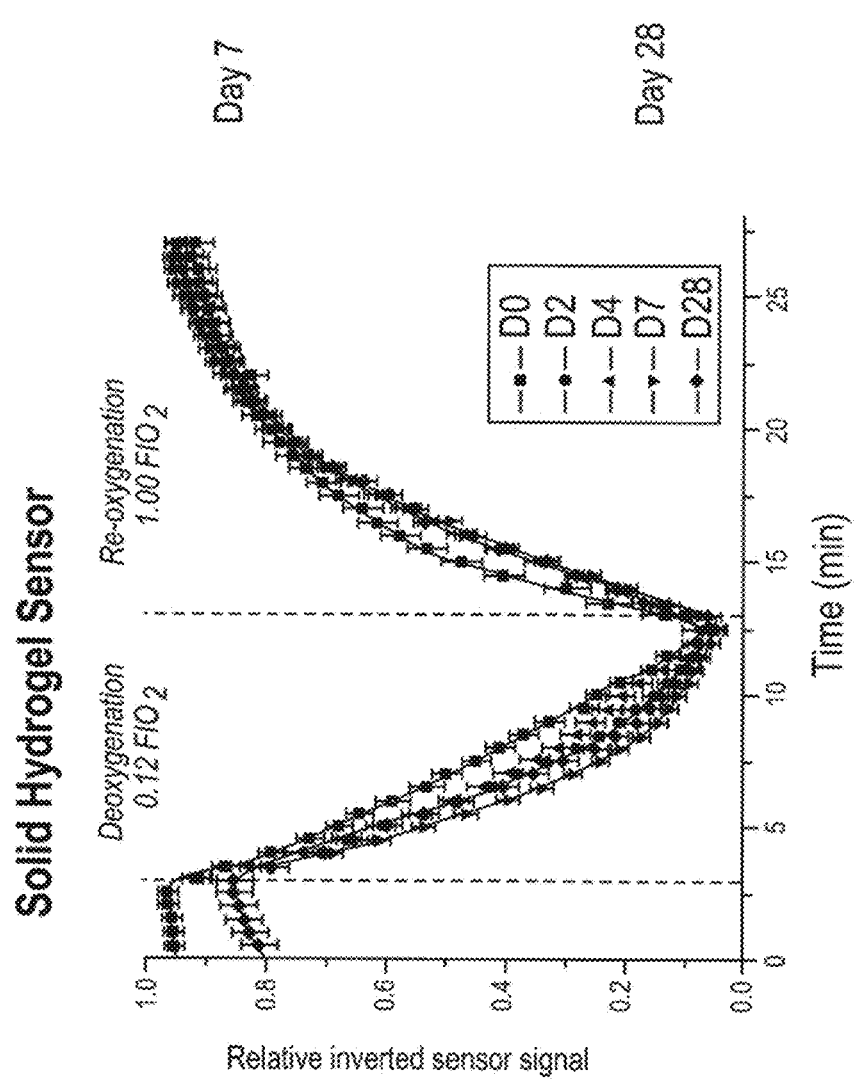
FIG. 11A depicts solid sensor response to deoxygenation (0.12 FIO2) and re-oxygenation (1.00 FIO2).

Rats were sacrificed and the sensors and surrounding tissue were explanted and frozen immediately in liquid nitrogen and stored at −80 C. Frozen tissue samples were cryosectioned at 10 µm thickness on a Leica CM1850 cryostat and mounted on poly L-lysine coated glass slides. Sections were immunostained for rat CD31 (BD Biosciences, San Jose, Calif.). Briefly, slides were fixed in acetone for 20 min at room temperature, rinsed in 1×PBS, blocked with staining buffer (5% normal donkey serum in 1×PBS) for 30 min, incubated with mouse-derived rat CD31 primary antibody at 1:200 in staining buffer for 1 h, and incubated with anti-mouse Alexa Fluor 488 (Jackson ImmunoResearch) for 30 min, and stained with Hoechst 33342 (Invitrogen) for 5 min at room temperature. Samples were fixed in 4% paraformaldehyde and imaged on the same day. Samples were fluorescently imaged using a Zeiss AxioSkop II+ fluorescence microscope equipped with a 12 bit CCD camera (QImaging) and an automated scanning stage (Marzhauser) driven by a Ludl Mac5000 driving unit (Ludl). An array of micrographs was acquired using a 5× objective (NA 0.25, Zeiss) and then stitched together to form a montage using Metamorph software. Exposures were set at low illumination intensities with 1×1 binning (pixel size of 1.36 µm×1.36 µm) and a typical acquisition period of 100 ms. The results of the experiment are depicted in FIG. 11.

Example 7: Measurement

Figure 2:
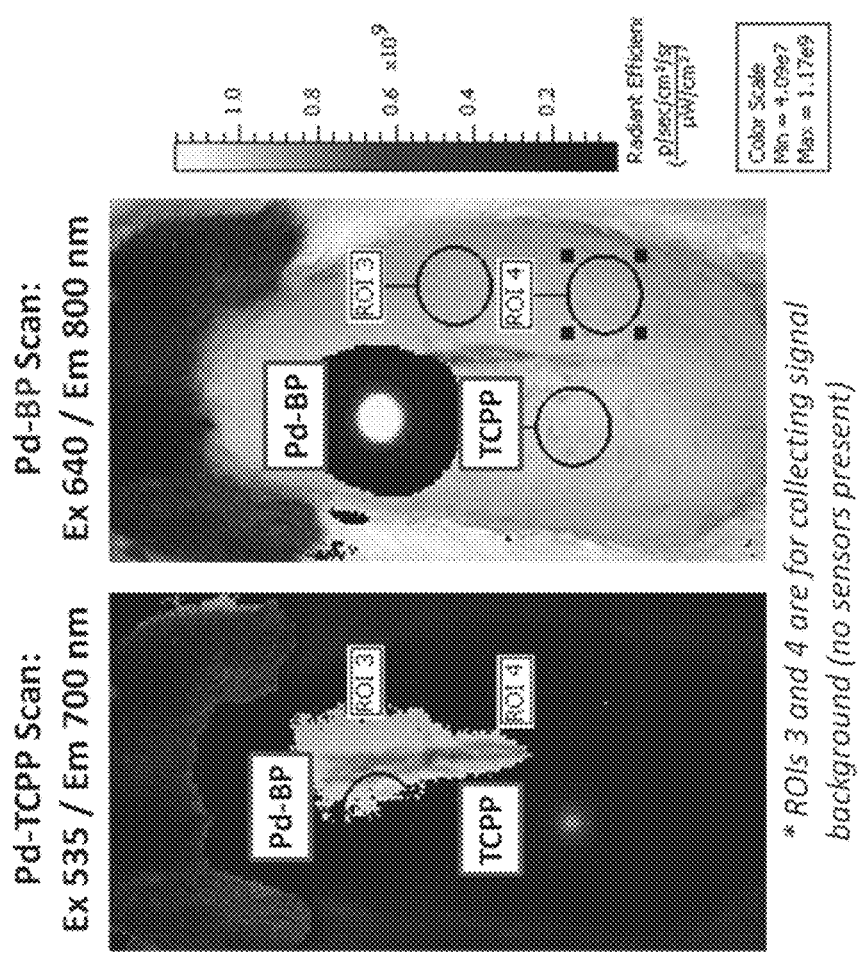
FIG. 2 demonstrates that Compound 2 (Pd-BP) incorporated into a pHEMA hydrogel sensor enables brighter signals from deeper within tissue.

Data from the sensor is collected by a fluorescent reader placed on the surface of skin directly above the sensor location, and the data is processed and displayed on a smart phone, other hand-held device, computer screen or other visualization format, for example using commercially available data display devices. Raw data is converted to an analyte concentration or some non-quantitative representation of the analyte concentration (e.g. high, low, within range). Values at any given point in time or trends (graphs over time) or summary statistics over a period of time are provided. An indication of the quality of the data is optionally provided. Hydrogels prepared from co-polymerization of HEMA with NIR Pd-BP and green-ex Pd-TCPP were subcutaneously implanted in a rat carcass, and their emission was measured (FIG. 2). Pd-BP was significantly brighter than Pd-TCPP due to the NIR excitation and emission wavelengths, which allow much greater light penetration into the skin, enabling deeper sensor placement. Deeper placement is desirable for better immunological response, but was not possible previously because the original green Pd-TCPP signal was largely blocked, e.g., scattered and/or absorbed, by the skin. Only shallow dermal implants were possible. Additionally, Pd-BP hydrogel sensors produced bright detectable signal when implanted deep under a mouse skull (inside mouse brain).

Example 8: Stability of Sensors Implanted in Rat Skin

Oxygen sensors were implanted in rat skin and the intensity of their signal was monitored for 170 days. FIG. 4 shows fluorescence of the sensor implanted in a mouse skin for 170 days. Intensity varied as a function of implantation depth (data was normalized to baseline fluorescence). Inhaled oxygen was modulated between 100% and 12% and images were collected every 30 s in a Caliper IVIS (Spectrum, Ex=640 nm, Em=800 nm, 20 nm bandwidth). Regions of interest (ROIs) were drawn around the sensors and the data plotted versus time (FIG. 6). This data illustrate that the sensors made with the dyes of the present invention maintain function for many months in vivo. Additionally, the tissue-integrating sensor was compared to a solid sensor. The tissue-integrating sensor produced a faster kinetic response to changes in oxygen levels than the solid sensor, which illustrates another advantageous property of the tissue-integrating sensor.

Example 9: In-Vitro Oxygen Detection in Low Oxygen Concentrations

Figures 8A, 8B:
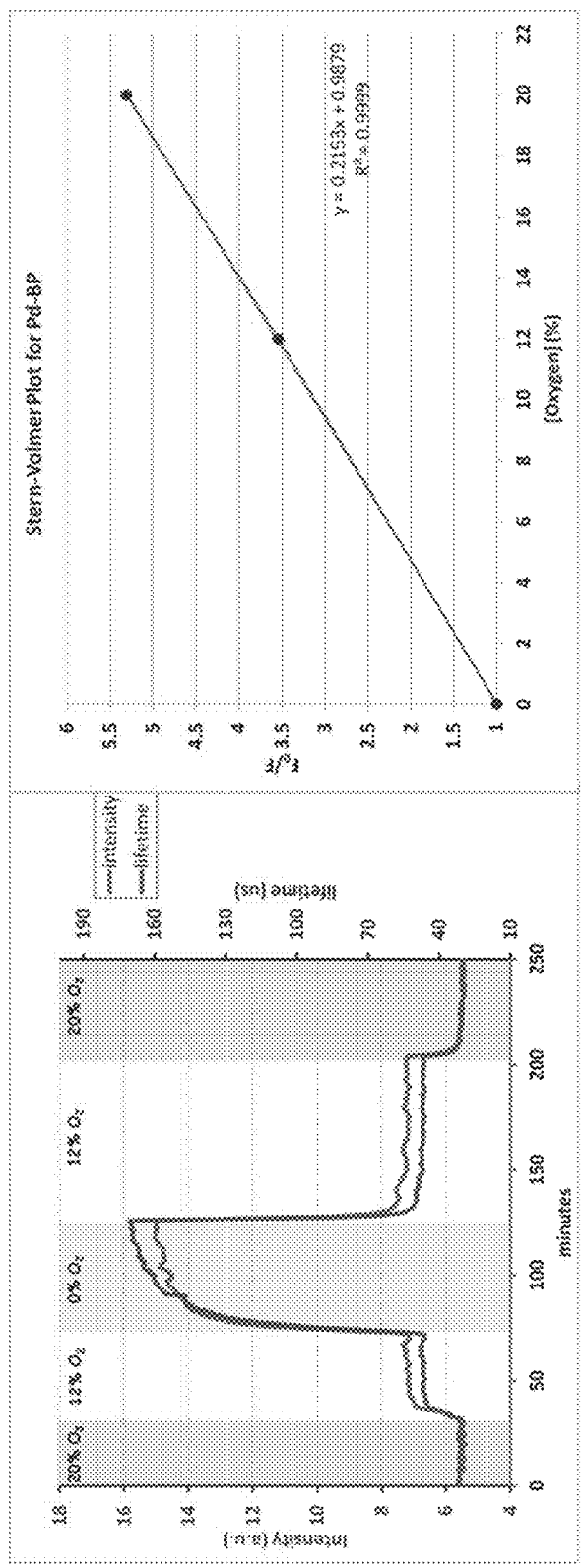
FIG. 8A depicts dynamic response of Pd-BP hydrogels to $O_2$. The response is linear with good sensitivity and rapid response time.
FIG. 8B depicts a Stern-Vomer plot of $O_2$ quenching efficiency with Pd-BP (B).

To characterize oxygen sensitivity of Pd-BP, the intensity and luminescence lifetime of the dye in a porous HEMA hydrogel at various $O_2$ levels (0%, 12%, and 20% O2) was measured (FIG. 8). The hydrogels were tested in a custom-built flow-through system (pH 7.4 PBS, 37° C.) while being monitored with the TauTheta fiber-optic instrument. The dye showed good reversibility, as well as good O₂ sensitivity as indicated by the Stern-Volmer plot.

Example 10: Preparation and Characterization of Glucose Sensor

Figures 9A, 9B:
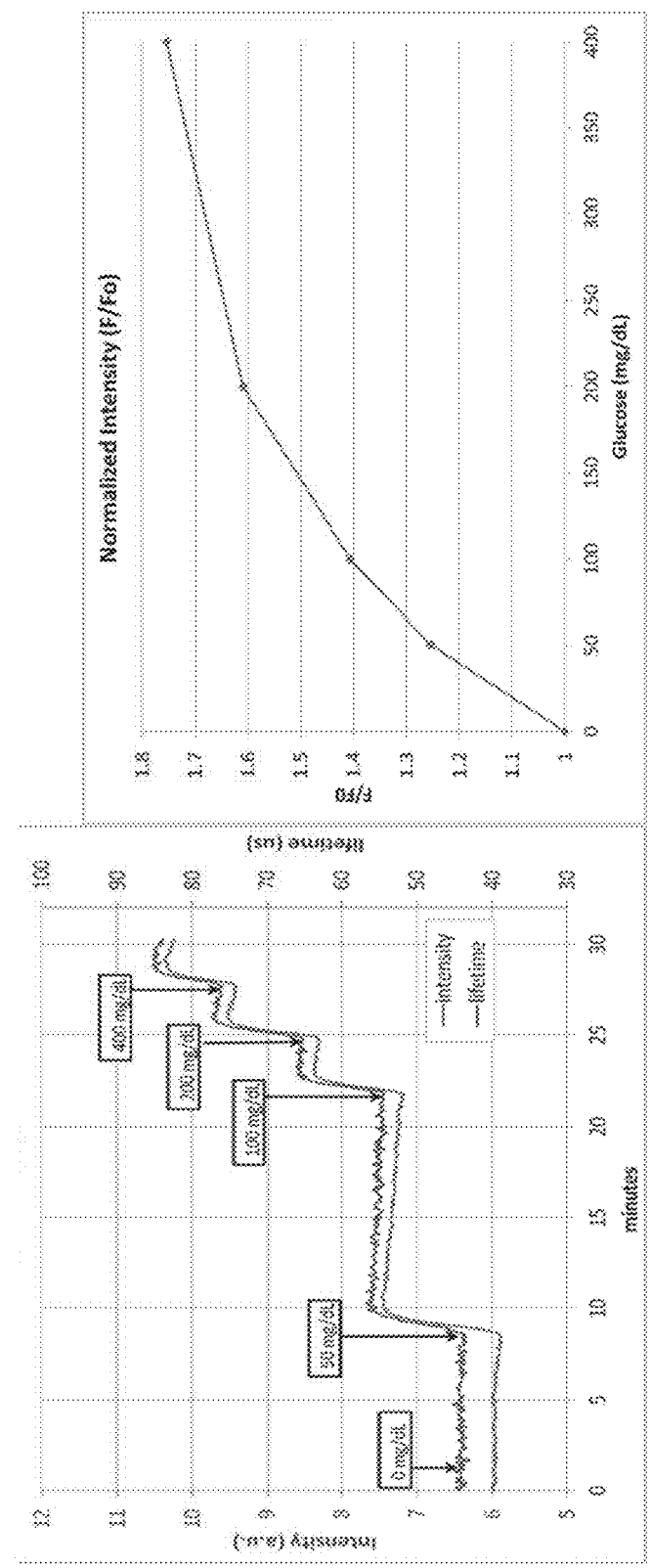
FIG. 9A depicts dynamic response of GOx/Pd-BP gel to glucose.
FIG. 9B depicts a normalized glucose dose-response curve.

Glucose oxidase (GOx) was entrapped in a pHEMA hydrogel containing covalently bound Pd-BP as described above. The porous morphology of the resulting sensor was confirmed with SEM (FIG. 5). The GOx-Pd-BP sensors were tested for glucose response in a flow-through system (PBS, 37° C.). The luminescence intensity and lifetime of Pd-BP within the gel were monitored during a series of glucose excursions spanning the physiological range (FIG. 9). The slight dip in intensity and lifetime during the plateaus (where glucose concentration was held constant) are due to consumption of glucose within the test reservoir by GOx.

Example 11: Implantation of O2 Sensor into Pig Skin

Figures 10A, 10B:
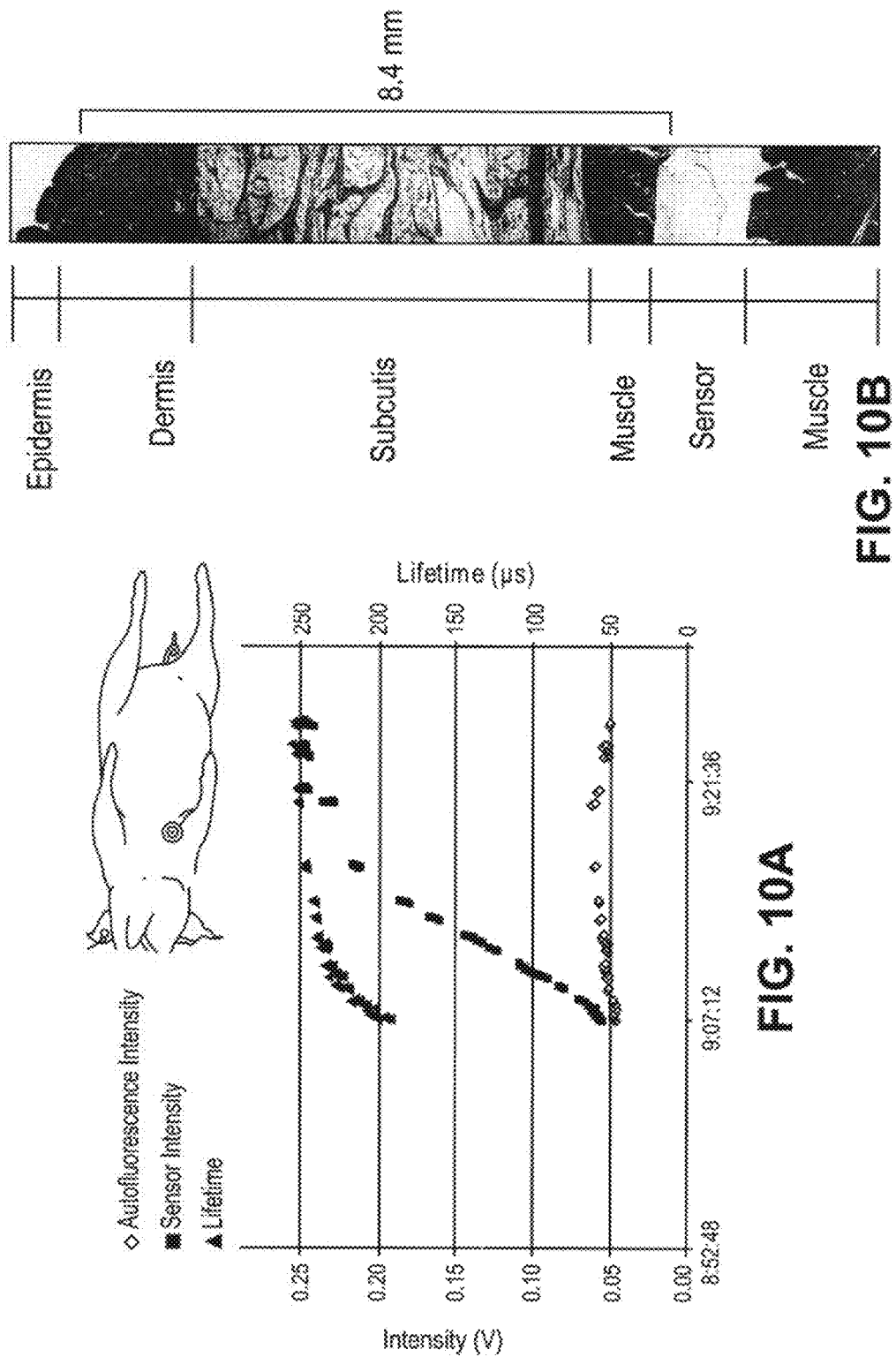
FIG. 10A depicts detectable modulating sensor signal from the $O_2$ sensor.
FIG. 10B depicts histological analysis of pig biopsy containing the sensor.

Explant specimens were obtained from acute pig experiment during which time the O₂ sensors prepared from the polymers comprising Compound 2 were injected into a pig. Sensor signals were obtained. Fluorescence lifetime and intensity measurements were collected. After sensor signal measurements were obtained, the pig was sacrificed and specimens were fixed in 10% Formalin and stained with Hematoxylin and Eosin (H&E). Images and depth measurements were obtained using a Nikon microscope at 40× magnification and the Infinity 11 microscopy camera and software (Version 6.1.0, Luminera Corp.) Sequential overlapping images were obtained to create the final composite images. FIG. 10 depicts a sensor that was found to have been implanted at 8 mm in depth under the surface of the skin. FIG. 10 shows that modulating sensor signal was still detectable at the depth of sensor implantation of 8 mm under the surface of the skin.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

All patents, patent applications and publications mentioned herein are hereby incorporated by reference in their entirety. Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A sensor for detecting an analyte comprising a polymer, wherein said polymer comprises one or more residues of a luminescent dye and one or more residues of 2-hydroxyethyl methacrylate (HEMA), wherein the luminescent dye is a compound having the formula:

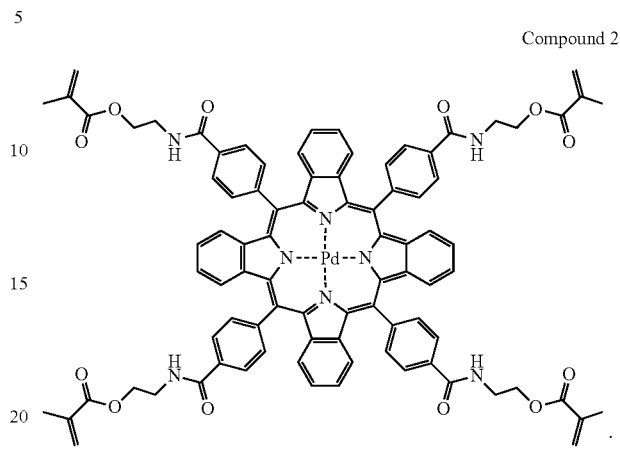

Compound 2

2. The sensor of claim 1 wherein the polymer is a hydrogel.
3. The sensor of claim 2 wherein the hydrogel further comprises one or more residues of tetraethyleneglycol dimethacrylate.
4. The sensor of claim 2 wherein the hydrogel further comprises one or more residues of triethyleneglycol dimethacrylate.
5. The sensor of claim 1 wherein the residue of the luminescent dye is present at a concentration from about 0.01 mM to about 5 mM.
6. The sensor of claim 1 wherein the residue of the luminescent dye is present at the concentration of about 1 mM.
7. The sensor of claim 1 wherein the analyte is oxygen.
8. The sensor of claim 1 wherein the sensor is tissue-integrating.
9. The sensor of claim 8 wherein the sensor generates detectable luminescent signal when placed under the skin of a mammalian subject.
10. The sensor of claim 9 wherein the sensor generates detectable luminescent signal when placed up to about 5 mm deep under the skin of a mammalian subject.
11. The sensor of claim 9 wherein the sensor generates detectable luminescent signal when placed more than 1 mm deep under the skin of a mammalian subject.
12. The sensor of claim 9 wherein the mammalian subject is a human.
13. The sensor of claim 9 wherein the sensor is stable in a mammalian tissue for longer than 1 week.
14. The sensor of claim 1 further comprising an oxidase.
15. The sensor of claim 14, wherein the oxidase is a glucose oxidase, ethanol oxidase, lactate oxidase, pyruvate oxidase, bilirubin oxidase, or histamine oxidase.
16. The sensor of claim 14 wherein the analyte is oxygen consumed by the oxidase.
17. The sensor of claim 16, wherein the oxidase is a glucose oxidase, ethanol oxidase, lactate oxidase, pyruvate oxidase, bilirubin oxidase, or histamine oxidase.
18. The sensor of claim 17 wherein the sensor is tissue-integrating.

* * * * *